US010216262B1

(12) United States Patent
Berme et al.

(10) Patent No.: US 10,216,262 B1
(45) Date of Patent: Feb. 26, 2019

(54) FORCE MANAGEMENT SYSTEM THAT INCLUDES A FORCE MEASUREMENT ASSEMBLY, A VISUAL DISPLAY DEVICE, AND ONE OR MORE DATA PROCESSING DEVICES

(71) Applicant: Bertec Corporation, Columbus, OH (US)

(72) Inventors: Necip Berme, Worthington, OH (US); Benjamin Robert Hoffman, Columbus, OH (US); Sasan Ghassab, Columbus, OH (US); Jaswandi Tushar Pitale, Hilliard, OH (US)

(73) Assignee: Bertec Corporation, Columbus, OH (US)

( * ) Notice: Subject to any disclaimer, the term of this patent is extended or adjusted under 35 U.S.C. 154(b) by 0 days.

(21) Appl. No.: 15/908,323

(22) Filed: Feb. 28, 2018

Related U.S. Application Data

(63) Continuation-in-part of application No. 15/242,558, filed on Aug. 21, 2016, now Pat. No. 9,916,011.
(Continued)

(51) Int. Cl.
*A61B 5/103* (2006.01)
*G06F 3/01* (2006.01)
*G06F 3/14* (2006.01)

(52) U.S. Cl.
CPC ............ *G06F 3/011* (2013.01); *A61B 5/1036* (2013.01); *G06F 3/012* (2013.01); *G06F 3/013* (2013.01);
(Continued)

(58) Field of Classification Search
CPC .... A65B 5/1036; G06F 3/147; G09G 2380/08
See application file for complete search history.

(56) References Cited

U.S. PATENT DOCUMENTS

| 5,205,800 A | 4/1993 | Grant |
| 5,611,174 A | 3/1997 | Hayashi |

(Continued)

FOREIGN PATENT DOCUMENTS

CN 201880270 * 6/2011

OTHER PUBLICATIONS

First office action on the merits (Non-Final Rejection) in U.S. Appl. No. 15/242,558, dated Oct. 24, 2016.
(Continued)

*Primary Examiner* — Ram A Mistry
(74) *Attorney, Agent, or Firm* — The Law Office of Patrick F. O'Reilly III, LLC

(57) ABSTRACT

A force measurement system includes a force measurement assembly with a top surface configured to receive at least one portion of the body of a subject and at least one force transducer configured to sense forces and/or moments being applied to the top surface; at least one visual display device having an output screen configured to at least partially circumscribe three sides of a torso of the subject, and one or more data processing devices operatively coupled to the force measurement assembly and the at least one visual display device. In one or more embodiments, the force measurement assembly may be in the form of an instrumented treadmill. In one or more further embodiments, the force measurement system may additionally comprise a motion capture system configured to detect the motion of one or more body gestures of the subject.

25 Claims, 23 Drawing Sheets

Related U.S. Application Data

(60) Provisional application No. 62/208,671, filed on Aug. 22, 2015.

(52) U.S. Cl.
CPC ............ *G06F 3/017* (2013.01); *G06F 3/1446* (2013.01); *G06F 2203/012* (2013.01)

(56) References Cited

U.S. PATENT DOCUMENTS

| | | | |
|---|---|---|---|
| 5,961,195 A * | 10/1999 | Yoshimatsu | G09B 9/058 353/122 |
| 6,038,488 A | 3/2000 | Barnes et al. | |
| 6,113,237 A | 9/2000 | Ober et al. | |
| 6,152,564 A | 11/2000 | Ober et al. | |
| 6,295,878 B1 | 10/2001 | Berme | |
| 6,354,155 B1 | 3/2002 | Berme | |
| 6,389,883 B1 | 5/2002 | Berme et al. | |
| 6,600,475 B2 * | 7/2003 | Gutta | G06F 3/0304 345/156 |
| 6,606,111 B1 * | 8/2003 | Kondo | H04N 7/15 348/14.01 |
| 6,738,065 B1 | 5/2004 | Even-Zohar | |
| 6,774,885 B1 | 8/2004 | Even-Zohar | |
| 6,936,016 B2 | 8/2005 | Berme et al. | |
| 6,944,581 B2 | 9/2005 | Creek | |
| 7,931,604 B2 | 4/2011 | Even-Zohar et al. | |
| 8,181,541 B2 | 5/2012 | Berme | |
| 8,315,822 B2 | 11/2012 | Berme et al. | |
| 8,315,823 B2 | 11/2012 | Berme et al. | |
| D689,388 S | 9/2013 | Berme | |
| D689,389 S | 9/2013 | Berme | |
| 8,543,540 B1 | 9/2013 | Wilson et al. | |
| 8,544,347 B1 | 10/2013 | Berme | |
| 8,643,669 B1 | 2/2014 | Wilson et al. | |
| 8,700,569 B1 | 4/2014 | Wilson et al. | |
| 8,704,855 B1 * | 4/2014 | Berme | A61B 5/1036 345/633 |
| 8,764,532 B1 | 7/2014 | Berme | |
| 8,847,989 B1 * | 9/2014 | Berme | G09G 5/12 345/633 |
| D715,669 S | 10/2014 | Berme | |
| 8,902,249 B1 | 12/2014 | Wilson et al. | |
| 8,915,149 B1 | 12/2014 | Berme | |
| 9,032,817 B2 | 5/2015 | Berme et al. | |
| 9,043,278 B1 | 5/2015 | Wilson et al. | |
| 9,066,667 B1 | 6/2015 | Berme et al. | |
| 9,081,436 B1 | 7/2015 | Berme et al. | |
| 9,168,420 B1 | 10/2015 | Berme et al. | |
| 9,173,596 B1 | 11/2015 | Berme et al. | |
| 9,200,897 B1 | 12/2015 | Wilson et al. | |
| 9,277,857 B1 | 3/2016 | Berme et al. | |
| D755,067 S | 5/2016 | Berme et al. | |
| 9,404,823 B1 | 8/2016 | Berme et al. | |
| 9,414,784 B1 | 8/2016 | Berme et al. | |
| 9,468,370 B1 | 10/2016 | Shearer | |
| 9,517,008 B1 | 12/2016 | Berme et al. | |
| 9,526,443 B1 | 12/2016 | Berme et al. | |
| 9,526,451 B1 | 12/2016 | Berme | |
| 9,558,399 B1 | 1/2017 | Jeka et al. | |
| 9,568,382 B1 | 2/2017 | Berme et al. | |
| 9,622,686 B1 | 4/2017 | Berme et al. | |
| 9,763,604 B1 | 9/2017 | Berme et al. | |
| 9,770,203 B1 | 9/2017 | Berme et al. | |
| 9,778,119 B2 | 10/2017 | Berme et al. | |
| 9,814,430 B1 | 11/2017 | Berme et al. | |
| 9,829,311 B1 | 11/2017 | Wilson et al. | |
| 9,854,997 B1 | 1/2018 | Berme et al. | |
| 2002/0149752 A1 * | 10/2002 | Courchesne | G03B 21/00 353/122 |
| 2003/0216656 A1 | 11/2003 | Berme et al. | |
| 2003/0223113 A1 * | 12/2003 | Starkweather | G03B 21/62 359/451 |
| 2005/0148432 A1 | 7/2005 | Carmein | |
| 2006/0264786 A1 * | 11/2006 | Nashner | A61B 5/1036 600/595 |
| 2008/0221487 A1 * | 9/2008 | Zohar | A61B 5/103 600/595 |
| 2008/0228110 A1 | 9/2008 | Berme | |
| 2010/0131113 A1 | 5/2010 | Even-Zohar | |
| 2011/0277562 A1 | 11/2011 | Berme | |
| 2012/0266648 A1 | 10/2012 | Berme et al. | |
| 2012/0271565 A1 | 10/2012 | Berme et al. | |
| 2013/0225370 A1 * | 8/2013 | Flynt | A63B 24/0087 482/4 |
| 2014/0274564 A1 | 9/2014 | Greenbaum | |
| 2015/0096387 A1 | 4/2015 | Berme et al. | |
| 2016/0245711 A1 | 8/2016 | Berme et al. | |
| 2016/0334288 A1 | 11/2016 | Berme et al. | |
| 2018/0024015 A1 | 1/2018 | Berme et al. | |

OTHER PUBLICATIONS

Second office action on the merits (Final Rejection) in U.S. Appl. No. 15/242,558, dated Feb. 24, 2017.

Third office action on the merits (Non-Final Rejection) in U.S. Appl. No. 15/242,558, dated May 26, 2017.

Fourth office action on the merits (Final Rejection) in U.S. Appl. No. 15/242,558, dated Aug. 15, 2017.

Notice of Allowance in U.S. Appl. No. 15/242,558, dated Oct. 30, 2017.

* cited by examiner

FORCE MANAGEMENT SYSTEM THAT INCLUDES A FORCE MEASUREMENT ASSEMBLY, A VISUAL DISPLAY DEVICE, AND ONE OR MORE DATA PROCESSING DEVICES

CROSS-REFERENCE TO RELATED APPLICATIONS

This is a continuation-in-part of U.S. Nonprovisional patent application Ser. No. 15/242,558 entitled "Force Measurement System That Includes A Force Measurement Assembly, A Visual Display Device, And One Or More Data Processing Devices", filed on Aug. 21, 2016, and further claims the benefit of U.S. Provisional Patent Application No. 62/208,671, entitled "Force Measurement System", filed on Aug. 22, 2015, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to force measurement systems. More particularly, the invention relates to a force measurement system that is capable of immersing a subject in a virtual reality environment.

2. Background and Description of Related Art

Force measurement systems are utilized in various fields to quantify the reaction forces and moments exchanged between a body and support surface. For example, in biomedical applications, force measurement systems are used for gait analysis, assessing balance and mobility, evaluating sports performance, and assessing ergonomics. In order to quantify the forces and moments resulting from the body disposed thereon, the force measurement system includes some type of force measurement device. Depending on the particular application, the force measurement device may take the form of a balance plate, force plate, jump plate, a force plate array, or some other device that is capable of quantifying the forces and moments exchanged between the body and the support surface.

Although, it is often difficult to accommodate conventional force measurement systems in the spaces of many buildings due to their expansive sizes. For example, a force plate array, which is often used as part of a gait lab in a building, typically occupies a considerable amount of floor space in the building. In addition to the difficulties associated with the space requirements for these systems, conventional force measurement systems are not capable of effectively immersing the subject being tested in a virtual reality environment, which may be used to simulate real-life scenarios that are encountered by the subject.

Therefore, what is needed is a force measurement system that includes an immersive visual display device that enables a subject being tested to become fully immersed in a virtual reality scenario or an interactive game. In addition, what is needed is a force measurement system that is capable of fully immersing a subject in a virtual reality environment, yet compact enough to fit in typical building spaces.

BRIEF SUMMARY OF EMBODIMENTS OF THE INVENTION

Accordingly, the present invention is directed to a force measurement system that substantially obviates one or more problems resulting from the limitations and deficiencies of the related art.

In accordance with one or more embodiments of the present invention, there is provided a force measurement system comprising a force measurement assembly configured to receive a subject, the force measurement assembly including a top surface for receiving at least one portion of the body of the subject; and at least one force transducer, the at least one force transducer configured to sense one or more measured quantities and output one or more signals that are representative of forces and/or moments being applied to the top surface of the force measurement assembly by the subject; at least one visual display device having an output screen configured to at least partially circumscribe three sides of a torso of the subject, the at least one visual display device configured to display one or more scenes on the output screen so that the scenes are viewable by the subject, wherein the one or more scenes are configured to create a simulated environment for the subject, and wherein the output screen of the at least one visual display device comprises a bottom edge and a top edge; and one or more data processing devices operatively coupled to the force measurement assembly and the at least one visual display device, the one or more data processing devices configured to receive the one or more signals that are representative of the forces and/or moments being applied to the top surface of the force measurement assembly by the subject, and to convert the one or more signals into output forces and/or moments, the one or more data processing devices further configured to dynamically increase or decrease a speed of one or more displaceable components of the force measurement system in accordance with a visual element of the one or more scenes that are displayed on the output screen of the at least one visual display device while the subject navigates through the one or more scenes of the simulated environment on the output screen of the at least one visual display device.

In a further embodiment of the present invention, the at least one visual display device comprises a concavely shaped projection screen having a cylindrical middle portion, a spherical bottom portion, and a spherical top portion, the cylindrical middle portion being disposed above the spherical bottom portion and below the spherical top portion, the cylindrical middle portion having a continuous curvature between first and second opposed side edges of the concavely shaped projection screen, wherein the cylindrical middle portion of the concavely shaped projection screen results in a focal region for a subject disposed on the force measurement assembly, rather than any one single focal point, so that an immersion experience for the subject is substantially unaffected by a height of the subject.

In yet a further embodiment, the concavely shaped projection screen comprises a plurality of screen sections that are attached to one another so as to form the overall screen.

In still a further embodiment, the force measurement assembly is in the form of an instrumented treadmill.

In yet a further embodiment, the force measurement system further comprises a motion base disposed underneath the instrumented treadmill, the motion base configured to displace the instrumented treadmill in one or more directions.

In still a further embodiment, the output screen of the at least one visual display device further comprises an overhanging top portion and a top cutout defining a cutout footprint; and the force measurement system further comprises a motion capture system operatively coupled to the one or more data processing devices, the motion capture system comprising at least one motion capture device configured to detect the motion of one or more body gestures of the subject, and the at least one motion capture device being disposed within the cutout footprint of the top cutout of the output screen of the at least one visual display device.

In yet a further embodiment, the at least one motion capture device comprises a plurality of motion capture devices, a subset of the plurality of motion capture devices being circumferentially spaced apart around the top cutout of the output screen of the at least one visual display device, and the subset of the plurality of motion capture devices being disposed within the cutout footprint.

In still a further embodiment, the one or more data processing devices are configured to adjust the one or more scenes on the output screen of the at least one visual display device in accordance with the detected motion of the one or more body gestures of the subject by the at least one motion capture device, wherein the one or more body gestures of the subject comprise at least one of: (i) one or more limb movements of the subject, (ii) one or more torso movements of the subject, and (iii) a combination of one or more limb movements and one or more torso movements of the subject.

In yet a further embodiment, the at least one motion capture device comprises a plurality of motion capture devices, and the plurality of motion capture devices of the motion capture system are in the form of a plurality of cameras, the plurality of cameras configured to capture the motion of the subject.

In still a further embodiment, a first subset of the plurality of cameras of the motion capture system are disposed above the subject, and wherein a second subset of the plurality of cameras of the motion capture system are disposed behind the subject.

In yet a further embodiment, the first subset of the plurality of cameras of the motion capture system are attached to the output screen of the at least one visual display device or to a screen support structure that supports the output screen of the at least one visual display device; and the second subset of the plurality of cameras of the motion capture system are attached to one of: (i) the output screen of the at least one visual display device, (ii) a screen support structure that supports the output screen of the at least one visual display device, and (iii) a camera mounting structure that is attached to the output screen of the at least one visual display device or to the screen support structure.

In still a further embodiment, the top surface of the force measurement assembly is disposed above the bottom edge of the output screen of the at least one visual display device, and the bottom edge of the output screen of the at least one visual display device is spaced apart from a floor on which the at least one visual display device is supported by one or more screen support members, the one or more screen support members being spaced apart from the top surface of the force measurement assembly that is configured to receive the at least one portion of the body of the subject.

In yet a further embodiment, the force measurement system further comprises an input device operatively coupled to the one or more data processing devices, the input device configured to enable the subject to select different navigation paths in the one or more scenes of the simulated environment on the output screen of the at least one visual display device.

In still a further embodiment, the input device that is configured to enable the subject to select different navigation paths in the one or more scenes of the simulated environment on the output screen of the at least one visual display device comprises an eye position tracking device or a head position tracking device.

In accordance with one or more other embodiments of the present invention, there is provided a force measurement system comprising a force measurement assembly configured to receive a subject, the force measurement assembly including one or more displaceable components, the one or more displaceable components having one or more respective surfaces for receiving one or more respective limbs of the subject; and at least one force transducer, the at least one force transducer configured to sense one or more measured quantities and output one or more signals that are representative of one or more loads being applied to the one or more respective surfaces of the one or more displaceable components by the subject; at least one visual display device having an output screen, the at least one visual display device configured to display a scene on the output screen so that the scene is viewable by the subject; a pointing or gaze direction determination device configured to determine a pointing direction or gaze direction of the subject, the pointing or gaze direction determination device being external to the at least one visual display device; and one or more data processing devices operatively coupled to the at least one force transducer of the force measurement assembly, the at least one visual display device, and the pointing or gaze direction determination device, the one or more data processing devices configured to receive the one or more signals that are representative of the forces and/or moments being applied to the one or more respective surfaces of the one or more displaceable components by the subject, and to convert the one or more signals into output forces and/or moments, the one or more data processing devices further configured to generate at least a first visual element and a second visual element, and to display the first visual element and the second visual element in the scene on the output screen of the at least one visual display device, the one or more data processing devices additionally configured to control the displacement of the one or more displaceable components of the force measurement assembly in accordance with the first visual element of the scene that is displayed on the output screen of the at least one visual display device, the one or more data processing devices further configured to determine a manner in which the subject interacts with the second visual element of the scene and to adjust the displacement of the one or more displaceable components of the force measurement assembly based upon the interaction of the subject with the second visual element during a subject testing or training routine, the second visual element of the scene that is displayed on the output screen of the at least one visual display device comprising at least one virtual target, and the one or more data processing devices additionally configured to determine the manner in which the subject interacts with the second visual element of the scene by determining when the pointing direction or the gaze direction of the subject, as determined by the pointing or gaze direction determination device, coincides with the at least one virtual target displayed on the output screen, and when the pointing direction of the subject does not coincide with the at least one virtual target displayed on the output screen. In these one or more other embodiments, when the pointing direction of the subject coincides with the at least one virtual target displayed on the output screen during the subject testing or training routine, the one or more data processing devices are further configured to maintain a current speed of the one or more displaceable components of the force measurement assembly. Also, in these one or more other embodiments, when the pointing direction of the subject does not coincide with the at least one virtual target displayed on the output screen during the subject testing or training routine, the one or more data processing devices are further configured to decrease the speed of the one or more displaceable components of the force measurement assembly below the current speed of the one or more displaceable components of the force measurement assembly so as to make it easier for the subject to properly focus on the at least one virtual target during the subject testing or training routine.

In a further embodiment of the present invention, the force measurement assembly is disposed on a motion base, the motion base configured to displace the force measurement assembly in one or more directions.

In yet a further embodiment, the force measurement assembly is in the form of an instrumented treadmill and the one or more displaceable components are in form of one or more treadmill displaceable elements of the instrumented treadmill; and the one or more data processing devices are further configured to adjust a rotational speed of the one or more treadmill displaceable elements in accordance with the first visual element of the scene that is displayed on the output screen of the at least one visual display device.

In still a further embodiment, the first visual element of the scene that is displayed on the output screen of the at least one visual display device comprises a ground surface element; and the one or more data processing devices are further configured to dynamically increase or decrease the rotational speed of the one or more treadmill displaceable elements in accordance with a type of the ground surface element of the scene that is displayed on the output screen of the at least one visual display device.

In yet a further embodiment, the first visual element of the scene that is displayed on the output screen of the at least one visual display device comprises an obstacle disposed in a virtual walking path of the subject; and the one or more data processing devices are further configured to dynamically decrease the rotational speed of the one or more treadmill displaceable elements when a virtual representation of the subject on the output screen collides with the obstacle disposed in the virtual walking path of the scene that is displayed on the output screen of the at least one visual display device.

In still a further embodiment, the virtual representation of the subject on the output screen of the at least one visual display device comprises an avatar controlled by one or more body gestures of the subject as detected by the force measurement assembly and a motion detection system.

In yet a further embodiment, the one or more data processing devices are further configured to compute a center of pressure for the subject as a function of the output forces and/or moments determined from the one or more signals of the force measurement assembly, and to control a movement of the virtual representation of the subject on the output screen of the at least one visual display device using the computed center of pressure.

In still a further embodiment, the pointing or gaze direction determination device comprises at least one of the following devices: (i) an eye position tracking device configured to track a position of one or more eyes of the subject, (ii) a head position tracking device configured to track a position of the head of the subject, and (iii) a pointing device configured to indicate an aiming direction of a body portion of the subject.

In yet a further embodiment, the one or more data processing devices are further configured to control a navigation of a virtual representation of the subject on the output screen of the at least one visual display device in accordance with an output signal from at least one of the eye position tracking device, the head position tracking device, and the pointing device.

In still a further embodiment, the at least one virtual target that is generated by the one or more data processing devices and displayed on the output screen of the at least one visual display device comprises a plurality of targets spaced apart on the output screen of the at least one visual display device; and the one or more data processing devices are further configured to determine whether the subject sequentially points in respective directions of each of the plurality of targets.

In yet a further embodiment, during the subject testing or training routine, when the pointing direction of the subject coincides with the at least one virtual target displayed on the output screen, the one or more data processing devices are further configured to set a target focus variable to a first value. In this further embodiment, during the subject testing or training routine, when the pointing direction of the subject does not coincide with the at least one virtual target displayed on the output screen, the one or more data processing devices are further configured to set the target focus variable to a second value that is different from the first value. Also, in this further embodiment, the one or more data processing devices are further configured to maintain the current speed of the one or more displaceable components of the force measurement assembly when the target focus variable equals the first value, and the one or more data processing devices are further configured to decrease the speed of the one or more displaceable components of the force measurement assembly below the current speed of the one or more displaceable components of the force measurement assembly when the target focus variable equals the second value.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which.

Throughout the figures, the same parts are always denoted using the same reference characters so that, as a general rule, they will only be described once.

DETAILED DESCRIPTION OF EMBODIMENTS OF THE INVENTION

Figure 1:
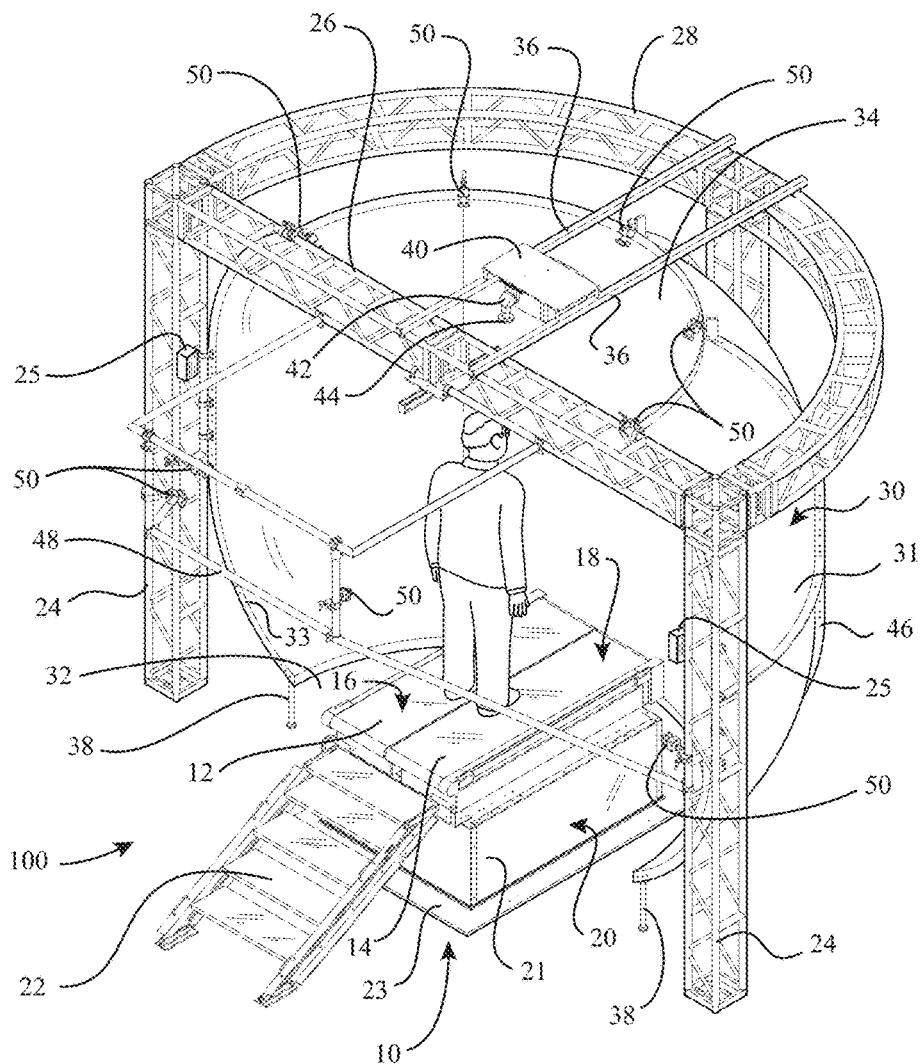
FIG. 1 is a perspective view of a force measurement system with a force measurement assembly in the form of an instrumented treadmill, according to a first embodiment of the invention.

A first embodiment of a force measurement system is seen generally at 100 in FIGS. 1-4. In the first illustrative embodiment, the force measurement system 100 generally comprises a force measurement assembly 10 in the form of an instrumented treadmill that is operatively coupled to a data acquisition/data processing device 60 (i.e., a data acquisition and processing device or computing device that is capable of collecting, storing, and processing data), which in turn, is operatively coupled to a subject visual display device 30 (see FIG. 9). The instrumented treadmill 10 is configured to receive a subject thereon. As best illustrated in FIG. 1, the instrumented treadmill 10 is attached to the top of a base subassembly 20. The instrumented treadmill 10 has a plurality of top surfaces (i.e., left and right rotating belts 12, 14) that are each configured to receive a portion of a body of a subject (e.g., the left belt 12 of the instrumented treadmill 10 is configured to receive a left leg of a subject, whereas the right belt 14 of the instrumented treadmill 10 is configured to receive a right leg of the subject).

In one or more embodiments, a subject walks or runs in an upright position atop the treadmill 10 with the feet of the subject contacting the respective top surfaces 16, 18 of the treadmill belts 12, 14. The belts 12, 14 of the treadmill 10 are rotated by independent electric actuator assemblies with speed adjustment mechanisms. In the illustrated embodiment, each electric actuator assembly and associated speed adjustment mechanism comprises an electric motor with a variable speed control device operatively coupled thereto. Each electric actuator assembly and associated speed adjustment mechanism is capable of rotating its respective treadmill belt 12, 14 at a plurality of different speeds. The speed adjustment mechanisms adjust the speed at which each of their respective treadmill belts 12, 14 are rotated. The speed adjustment mechanisms of the instrumented treadmill 10 are operatively coupled to a programmable logic controller (PLC) 58 (see FIG. 9). The programmable logic controller 58 of the instrumented treadmill 10 is operatively connected to the data acquisition/data processing device 60 by an electrical cable. While they are not readily visible in the perspective view of FIG. 1 due to their location, the instrumented treadmill 10 includes a plurality of force transducers (e.g., four (4) pylon-type force transducers 56—see e.g., FIG. 6) disposed below each rotating belt 12, 14 of the treadmill 10 so that the loads being applied to the top surfaces of the belts 12, 14 can be measured. Advantageously, the separated belts 12, 14 of the instrumented treadmill 10 enable the forces and/or moments applied by the left and right legs of the subject to be independently determined. The pylon-type force transducers 56 of the instrumented treadmill 10 are also operatively coupled to the treadmill programmable logic controller 58 by an electrical cable. In turn, the treadmill programmable logic controller 58 is operatively coupled to the data acquisition/data processing device 60 so that the force and moment output data of the pylon-type force transducers 56 is capable of being analyzed and processed by the data acquisition/data processing device 60.

Figure 6:
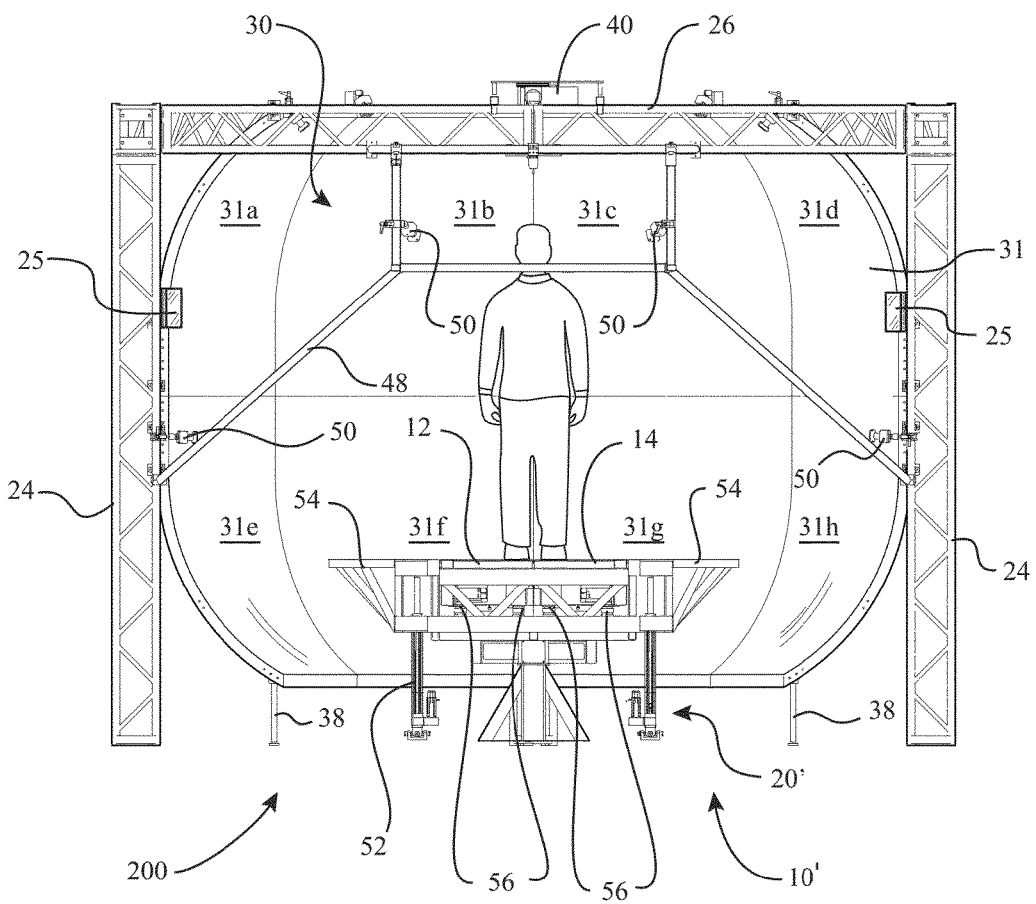
FIG. 6 is a front view of the force measurement system of FIG. 5.
Figure 7:
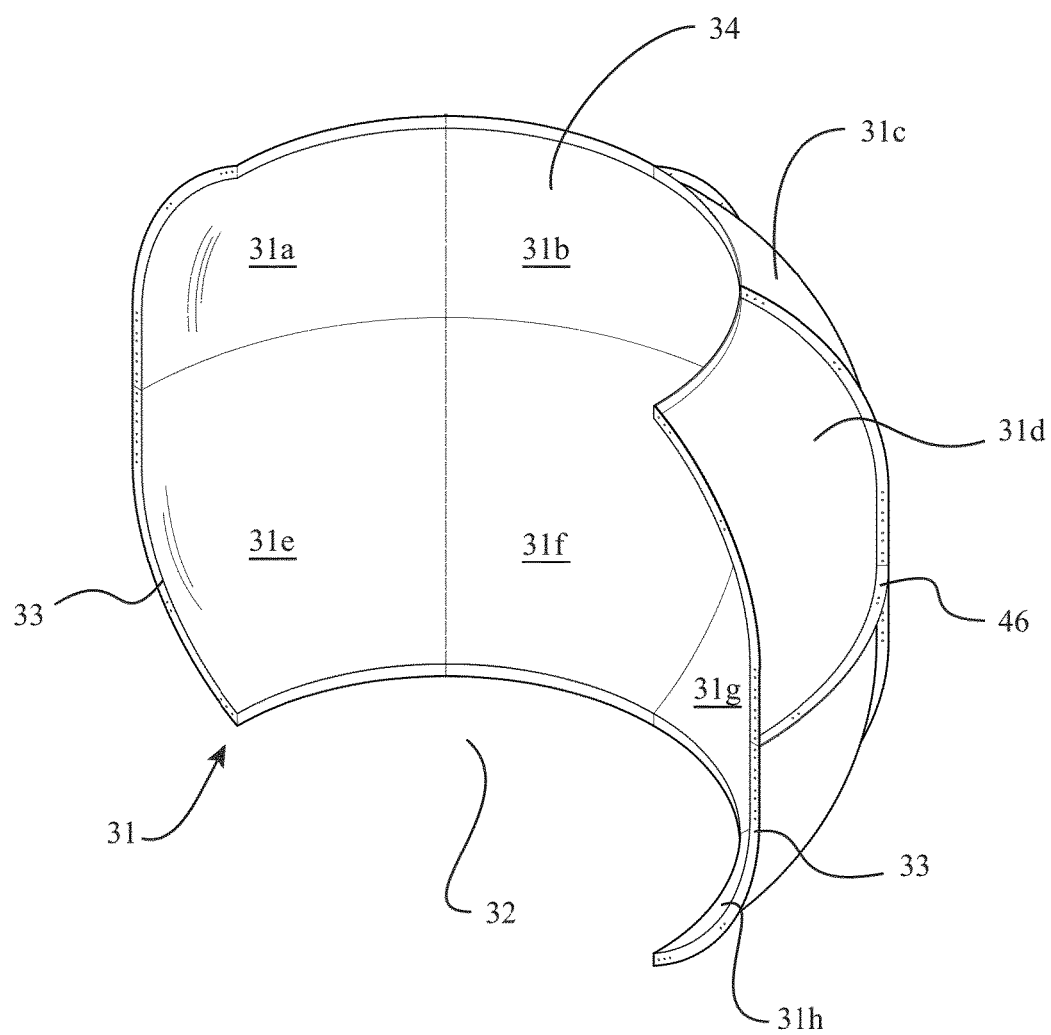
FIG. 7 is a perspective view of a concave projection screen of the force measurement systems of FIGS. 1 and 5.
Figure 8:
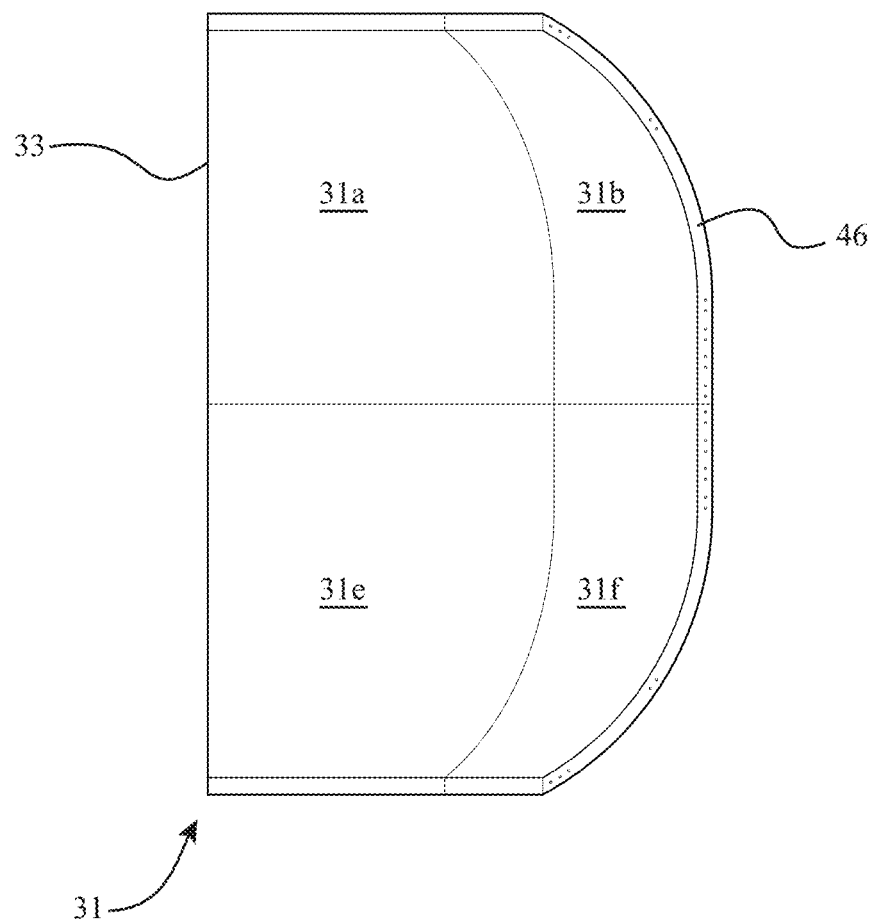
FIG. 8 is a longitudinal sectional view of the concave projection screen of FIG. 7.

As mentioned above, each of the treadmill belts 12, 14 is supported atop four (4) pylon-type force transducers 56 (or pylon-type load cells) that are disposed underneath, and near each of the four corners (4) of the left rotating belt 12 of the treadmill 10 and each of the four corners (4) of the right rotating belt 14 (see e.g., FIG. 6). Each of the eight (8) pylon-type force transducers 56 has a plurality of strain gages adhered to the outer periphery of a cylindrically-shaped force transducer sensing element for detecting the mechanical strain of the force transducer sensing element imparted thereon by the force(s) applied to the belt surfaces 16, 18 of the instrumented treadmill 10. In the first embodiment, each of the four (4) sets of pylon-type force transducers 56 are mounted atop the base subassembly 20. As best shown in the perspective view of FIG. 1, the base subassembly 20 comprises an upper body portion 21 and a lower base plate 23 disposed underneath the upper body portion 21. The instrumented treadmill 10 is also provided with a stair 22 connected thereto so as to facilitate access to the treadmill 10 by the subject. In the illustrative embodiment, the upper body portion 21 of the base subassembly 20 is provided with an aluminum honeycomb core disposed therein so as to enable the base subassembly 20 to be very stiff without adding excessive weight.

In an alternative embodiment, rather than using four (4) pylon-type force transducers 56 on each treadmill belt assembly 12, 14, force transducers in the form of transducer beams could be provided under each treadmill belt assembly 12, 14. In this alternative embodiment, the left treadmill belt assembly 12 could comprise two transducer beams that are disposed underneath, and on generally opposite sides of the treadmill belt assembly 12. Similarly, in this embodiment, the right treadmill belt assembly 14 could comprise two transducer beams that are disposed underneath, and on generally opposite sides of the right treadmill belt assembly 14. Similar to the pylon-type force transducers 56, the force transducer beams could have a plurality of strain gages attached to one or more surfaces thereof for sensing the mechanical strain imparted on the beam by the force(s) applied to the surfaces 16, 18 of the instrumented treadmill 10.

Rather, than using four (4) force transducer pylons under each treadmill belt assembly 12, 14, or two spaced-apart force transducer beams under each treadmill belt assembly 12, 14, it is to be understood that the instrumented treadmill 10 can also utilize the force transducer technology described in U.S. Pat. No. 8,544,347, the entire disclosure of which is incorporated herein by reference.

In the illustrated embodiment, the electrical cable mentioned above is used for the transmission of data between the instrumented treadmill 10 and the data acquisition/data processing device 60. A separate power cable is used to provide power to the instrumented treadmill 10 (e.g., a power cable connected directly to the electrical power system of the building in which the treadmill 10 is disposed). While a hardwired data connection is provided between the instrumented treadmill 10 and the data acquisition/data processing device 60 in the illustrative embodiment, it is to be understood that the instrumented treadmill 10 can be operatively coupled to the data acquisition/data processing device 60 using other signal transmission means, such as a wireless data transmission system.

Figure 9:
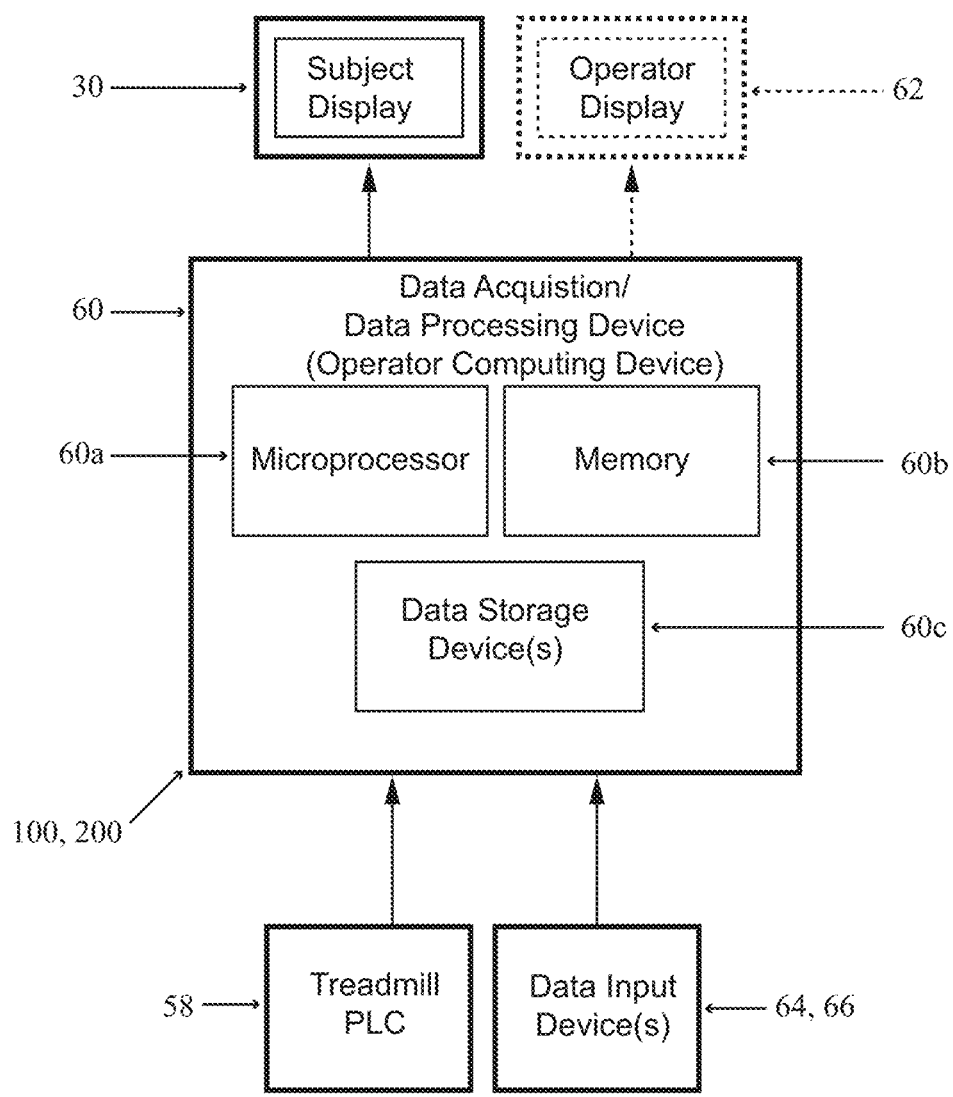
FIG. 9 is a block diagram of constituent components of the force measurement system with a force measurement assembly in the form of an instrumented treadmill, according to an embodiment of the invention.

Now, turning to FIG. 9, it can be seen that the illustrated data acquisition/data processing device 60 (i.e., the operator computing device) of the force measurement system 100 includes a microprocessor 60a for processing data, memory 60b (e.g., random access memory or RAM) for storing data during the processing thereof, and data storage device(s) 60c, such as one or more hard drives, compact disk drives, floppy disk drives, flash drives, or any combination thereof.

As shown in FIG. 9, the programmable logic controller (PLC) 58 of the instrumented treadmill 10, and the subject visual display device 30 are operatively coupled to the data acquisition/data processing device 60 such that data is capable of being transferred between these devices 30, 58, and 60. Also, as illustrated in FIG. 9, a plurality of data input devices 64, 66, such as a keyboard and mouse, are diagrammatically shown in FIG. 9 as being operatively coupled to the data acquisition/data processing device 60 so that a user is able to enter data into the data acquisition/data processing device 60. Also, as depicted in FIG. 9, an operator visual display device 62 may also be operatively coupled to the data acquisition/data processing device 60 so that an operator (e.g., clinician) of the force measurement system 100 has a more convenient dedicated display, and thus, is not required to use the subject visual display device 30. In some embodiments, the data acquisition/data processing device 60 can be in the form of a desktop computer, while in other embodiments, the data acquisition/data processing device 60 can be embodied as a laptop computer.

Advantageously, the programmable logic controller 58 (see e.g., FIG. 9, which is a type of data processing device) provides real-time control of the treadmill actuators (i.e., motors) that control the rotation of the left and right treadmill belts 12, 14. The real-time control provided by the programmable logic controller 58 ensures that the software regulating the control of the left and right treadmill belts 12, 14 operates at the design clock rate, thereby providing fail-safe operation for subject safety. In one embodiment, the programmable logic controller 58 comprises both the treadmill control software and the input/output management software, which controls the functionality of the input/output (I/O) module of the programmable logic controller 58. In one embodiment, the programmable logic controller 58 utilizes EtherCAT protocol for enhanced speed capabilities and real-time control.

In one or more embodiments, the input/output (I/O) module of the programmable logic controller 58 allows various accessories to be added to the force measurement system 100. For example, an eye movement tracking system, such as that described by U.S. Pat. Nos. 6,113,237 and 6,152,564 could be operatively connected to the input/output (I/O) module of the programmable logic controller 58. As another example, a head movement tracking system, which is instrumented with one or more accelerometers, could be operatively connected to the input/output (I/O) module.

In one or more embodiments, an emergency stop switch may be operatively coupled to the programmable logic controller 58 in order to quasi-instantaneously stop the rotation of the treadmill belts 12, 14. As such, the emergency stop switch is a safety mechanism that protects a subject disposed on the instrumented treadmill 10 from potential injury. In an exemplary embodiment, the emergency stop switch may be in the form of a red pushbutton that can be easily pressed by a user of the force measurement system 100 in order to stop the rotation of the treadmill belts 12, 14.

Now, the acquisition and processing of the load data carried out by the force measurement system will be described. Initially, a load is applied to the instrumented treadmill 10 by a subject disposed thereon. The load is transmitted from the treadmill belt assemblies 12, 14 to its respective set of pylon-type force transducers 56 (or force transducer beams). As described above, in the illustrated embodiment, each treadmill belt assembly 12, 14 comprises four (4) pylon-type force transducers 56 disposed thereunder. Preferably, these pylon-type force transducers 56 are disposed near respective corners of each treadmill belt assembly 12, 14. In a preferred embodiment, each of the pylon-type force transducers 56 includes a plurality of strain gages wired in one or more Wheatstone bridge configurations, wherein the electrical resistance of each strain gage is altered when the associated portion of the associated pylon-type force transducer undergoes deformation resulting from the load (i.e., forces and/or moments) acting on the treadmill belt assemblies 12, 14. For each plurality of strain gages disposed on the pylon-type force transducers 56, the change in the electrical resistance of the strain gages brings about a consequential change in the output voltage of the Wheatstone bridge (i.e., a quantity representative of the load being applied to the measurement surface). Thus, in one embodiment, the four (4) pylon-type force transducers 56 disposed under each treadmill belt assembly 12, 14 output a total of thirty-two (32) raw output voltages (signals) in either analog or digital form. In some embodiments, if the output voltages (signals) are in analog form, the thirty-two (32) raw output voltages (signals) from each treadmill belt assembly 12, 14 are then transmitted to a preamplifier board for preconditioning. The preamplifier board is used to increase the magnitudes of the transducer analog voltages. After which, in one or more embodiments, the analog output signals $S_{APO1}$-$S_{APO32}$ are transmitted from the analog preamplifier to the treadmill programmable logic controller (PLC) 58. In the treadmill programmable logic controller 58, the analog output signals $S_{APO1}$-$S_{APO32}$ are converted into forces, moments, centers of pressure (COP), subject center of gravity (COG), and/or sway angle for the subject. Then, the forces, moments, centers of pressure (COP), subject center of gravity (COG), and/or sway angle for the subject computed by the programmable logic controller 58 are transmitted to the data acquisition/data processing device 60 (operator computing device 60) so that they can be utilized for analyzing the movement of the subject and/or for reports displayed to an operator or clinician. Also, in yet another embodiment, the preamplifier board additionally could be used to convert the analog voltage signals into digital voltage signals (i.e., the preamplifier board could be provided with an analog-to-digital converter). In this embodiment, digital voltage signals would be transmitted to the treadmill programmable logic controller 58 rather than analog voltage signals.

In one or more embodiments, when the programmable logic controller 58 receives the voltage signals $S_{ACO1}$-$S_{ACO32}$, it initially transforms the signals into output forces and/or moments by multiplying the voltage signals $S_{ACO1}$-$S_{ACO32}$ by a calibration matrix. After which, the force and moment components (i.e., $F_{Lx}$, $F_{Ly}$, $F_{Lz}$, $M_{Lx}$, $M_{Ly}$, $M_{Lz}$) exerted on the left belt surface 16 of the left treadmill belt assembly 12 by the left foot of the subject, the force and moment components (i.e., $F_{Rx}$, $F_{Ry}$, $F_{Rz}$, $M_{Rx}$, $M_{Ry}$, $M_{Rz}$) exerted on the right belt surface 18 of the right treadmill belt assembly 14 by the right foot of the subject, and the center of pressure ($x_{P_L}$, $y_{P_L}$; $x_{P_R}$, $y_{P_R}$) for each foot of the subject (i.e., the x and y coordinates of the point of application of the force applied to the measurement surface by each foot) are determined by the programmable logic controller 58, and then transmitted to the data acquisition/data processing device 60.

Now, with reference to FIGS. 1-4, the subject visual display device 30 of the force measurement system 100 will be described in more detail. In the illustrated embodiment, the subject visual display device 30 generally comprises a projector 40 with a fisheye lens 44, and a concave projection screen 31 with a cylindrical middle portion and spherical top and bottom portions. In other words, in the illustrative embodiment, the projection screen 31 of the force measurement system 100 is not entirely spherically-shaped or dome-shaped. Advantageously, because the concave projection screen 31 is cylindrical in the middle with spherical parts on the top and bottom, a focal line is created for the subject standing on the instrumented treadmill 10, rather than a single focal point which would be created if the screen 31 were entirely spherical in shape. Thus, advantageously, individuals of different heights may be accommodated within the confines of the concave projection screen 31 without adversely affecting the focal region during the immersion (i.e., the height of a subject does not materially affect the immersive effect of the concave projection screen 31).

Figure 2:
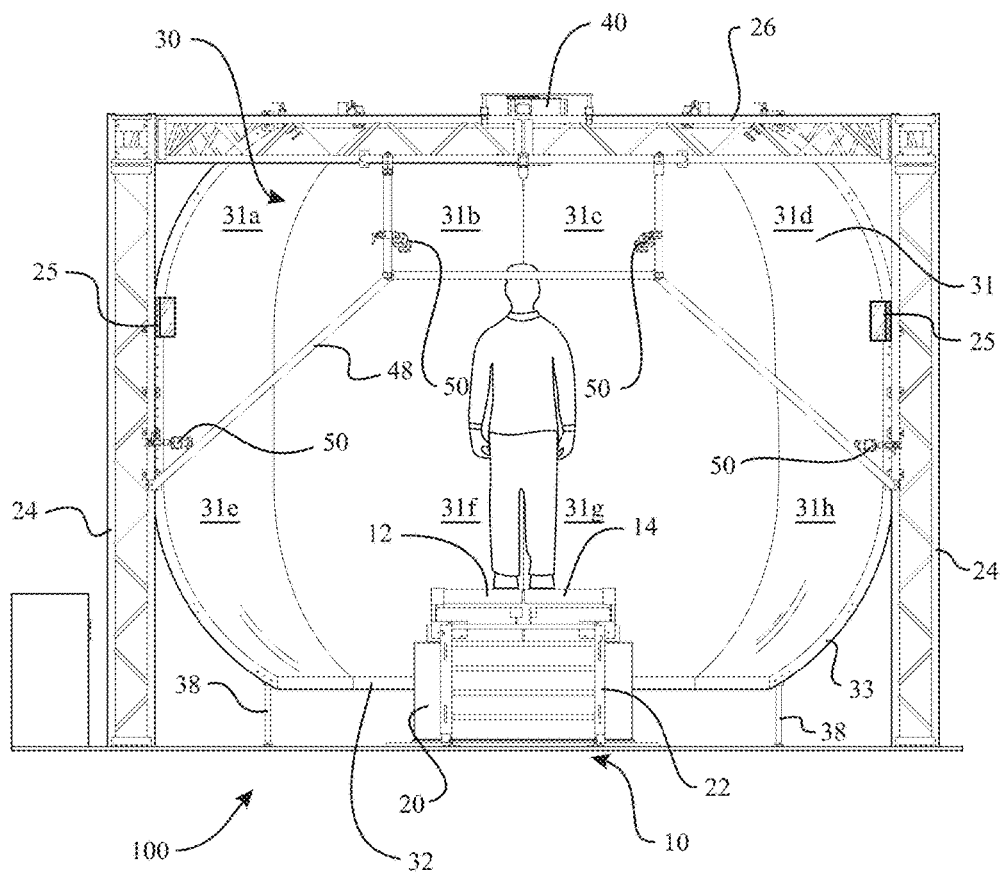
FIG. 2 is a front view of the force measurement system of FIG. 1.

Turning again to the illustrative embodiment of FIGS. 1-4, the projector 40 with the fisheye-type lens 44 projects a light beam through a semi-circular cutout 34 in the top of the concave projection screen 31. In FIG. 1, it can be seen that the fisheye lens 44 is connected to the body of the projector 40 by an elbow fitting 42. Also, as best shown in FIGS. 1 and 2, the concave projection screen 31 may be provided with a peripheral flange 33 therearound. Advantageously, the concave projection screen 31 is a continuous curved surface that does not contain any lines or points resulting from the intersection of adjoining planar or curved surfaces (i.e., all section seams in the screen 31 may be filled so as to form a continuous curved surface facing the subject). Thus, the projection screen 31 is capable of creating a completely immersive visual environment for a subject being tested on the instrumented treadmill 10 because the subject is unable to focus on any particular reference point or line on the screen 31. As such, the subject becomes completely immersed in the virtual reality scene(s) being projected on the concave projection screen 31, and thus, his or her visual perception can be effectively altered during a test being performed using the force measurement system 100 (e.g., a balance test). In order to permit a subject to be substantially circumscribed by the generally hemispherical projection screen 31 on three sides, the bottom of the screen 31 is provided with a semi-circular cutout 32 in the illustrative embodiment. While the concave projection screen 31 thoroughly immerses the subject in the virtual reality scene(s), it advantageously does not totally enclose the subject. Totally enclosing the subject could cause him or her to become extremely claustrophobic. Also, the clinician would be unable to observe the subject or patient in a totally enclosed environment. As such, the illustrated embodiment of the force measurement system 100 does not utilize a totally enclosed environment, such as a closed, rotating shell, etc. Also, the subject visual display device 30 is not attached to the subject, and it is spaced apart from the instrumented treadmill 10.

In one embodiment of the invention, the generally hemispherical projection screen 31 is formed from a suitable material (e.g., an acrylic, fiberglass, fabric, aluminum, etc.) having a matte gray color. A matte gray color is preferable to a white color because it minimizes the unwanted reflections that can result from the use of a projection screen having a concave shape. Also, in an exemplary embodiment, the projection screen 31 has a diameter (i.e., width $W_S$) of approximately 180 inches and a depth $D_S$ of approximately 90 inches. Although, those of ordinary skill in the art will readily appreciate that other suitable dimensions may be utilized for the projection screen 31, provided that the selected dimensions for the screen 31 are capable of creating an immersive environment for a subject disposed on the instrumented treadmill 10 (i.e., the screen 31 of the subject visual display device 30 engages enough of the subject's peripheral vision such that the subject becomes, and remains immersed in the virtual reality scenario). In one or more embodiments, the projection screen 31 fully encompasses the peripheral vision of the subject (e.g., by the coronal plane CP of the subject being disposed inwardly from the flange 33 within the confines of the screen 31). In other words, the output screen 31 of the at least one visual display 30 at least partially circumscribes three sides of a subject. The overhanging top portion of the projection screen 31 creates an efficient manner in which to fully immerse the subject. If the projection screen 31 were not formed with the overhanging top portion, the height of the projection screen 31 would have to be greatly increased in order to create the same full immersive effect. As such, the use of the concave projection screen 31 with the spherical, overhanging top portion allows the screen 31 to be much shorter, while still achieving the desired effect of the total immersion of the subject.

Figure 4:
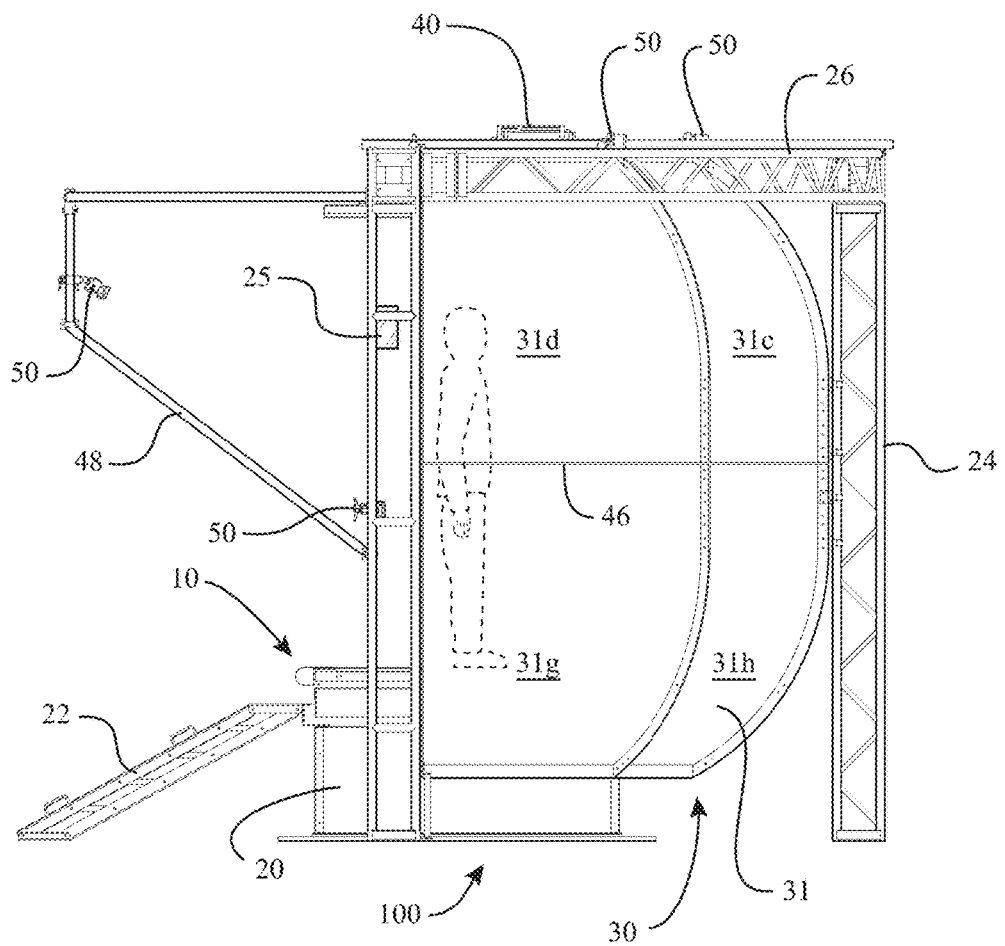
FIG. 4 is a side view of the force measurement system of FIG. 1.

With particular reference to FIGS. 1, 2, and 4, it can be seen that, in the illustrated embodiment, the concave projection screen 31 of the at least one visual display 30 is formed from a plurality of sections 31a-31h. Specifically, in the illustrative embodiment, referring initially to the front view of FIG. 2, it can be seen that the concave projection screen 31 comprises a first top left end section 31a, a second top left middle section 31b, a third top right middle section 31c, a fourth top right end section 31d, a fifth bottom left end section 31e, a sixth bottom left middle section 31f, a seventh bottom right middle section 31g, and an eighth bottom right end section 31h. As shown in FIG. 1, each of these screen sections 31a-31h comprises one or more connector flanges 46 that are used to connect the screen sections 31a-31h to one another (e.g., the screen sections 31a-31h are bolted to one another). Advantageously, forming the concave projection screen 31 from a plurality of separate, interconnectable sections 31a-31h allows the concave projection screen 31 to be more easily installed inside the room of a building because the screen 31 can be transported in sections 31a-31h, and then subsequently installed once it is inside the room (i.e., the sections 31a-31h may be connected together once inside the room). As such, the sectional construction of the concave projection screen 31 obviates the need for a large opening (e.g., a door opening) into the room in which the screen 31 is being installed.

In a preferred embodiment, the data acquisition/data processing device 60 is configured to convert a two-dimensional (2-D) image, which is configured for display on a conventional two-dimensional screen, into a three-dimensional (3-D) image that is capable of being displayed on the hemispherical output screen 31 without excessive distortion. That is, the data acquisition/data processing device 60 executes a software program that utilizes a projection mapping algorithm to "warp" a flat 2-D rendered projection screen image into a distorted 3-D projection image that approximately matches the curvature of the final projection surface (i.e., the curvature of the hemispherical output screen 31), which takes into account the distortion of the lens 44 of the projector 40. In particular, the projection mapping algorithm utilizes a plurality of virtual cameras and projection surfaces (which are modeled based upon the actual projection surfaces) in order to transform the two-dimensional (2-D) images into the requisite three-dimensional (3-D) images. Thus, the projector lens 44 information and the concave projection screen 31 dimensional data are entered as inputs into the projection mapping algorithm software. When a human subject is properly positioned in the confines of the hemispherical output screen 31, he or she will see a representation of the virtual reality scene wrapping around them instead of only seeing a small viewing window in front of him or her. Advantageously, using a software package comprising a projection mapping algorithm enables the system 100 to use previously created 3-D modeled virtual worlds and objects without directly modifying them. Rather, the projection mapping algorithm employed by the software package merely changes the manner in which these 3-D modeled virtual worlds and objects are projected into the subject's viewing area.

As described above, with reference to FIG. 1, it can be seen that the fisheye lens 44 of the projector 40 is connected to the body of the projector 40 by an elbow fitting 42. In other words, the fisheye lens 44 is disposed at a non-zero, angled orientation relative to a body of the projector 40. In the illustrated embodiment, the non-zero, angled orientation at which the fisheye lens 44 is disposed relative to the body of the projector 40 is approximately 90 degrees. The elbow fitting 42 comprises a one-way mirror disposed therein for changing the direction of the light beam emanating from the projector 40. As illustrated in FIG. 1, the fisheye lens 44 is disposed at approximately the apex of the concave projection screen 31, and it extends down through the cutout 34 at the top of the screen 31.

Those of ordinary skill in the art will also appreciate that the subject visual display device 31 may utilize other suitable projection means. For example, rather using an overhead-type projector 40 as illustrated in FIGS. 1-4, a direct or rear projection system can be utilized for projecting the image onto the screen 31, provided that the direct projection system does not interfere with the subject's visibility of the target image. In another alternative embodiment, two projectors, each having a respective fisheye-type lens, are used to project an image onto the screen 31. In this alternative embodiment, the two projectors with respective fisheye-type lens project intersecting light beams through the cutout 34 in the top of the generally hemispherical projection screen 31. Advantageously, the use of two projectors with respective fisheye-type lens, rather than just a single projector 40 with a fisheye lens 44, has the added benefit of removing shadows that are cast on the output screen 31 by the subject disposed on the instrumented treadmill 10.

Figure 3:
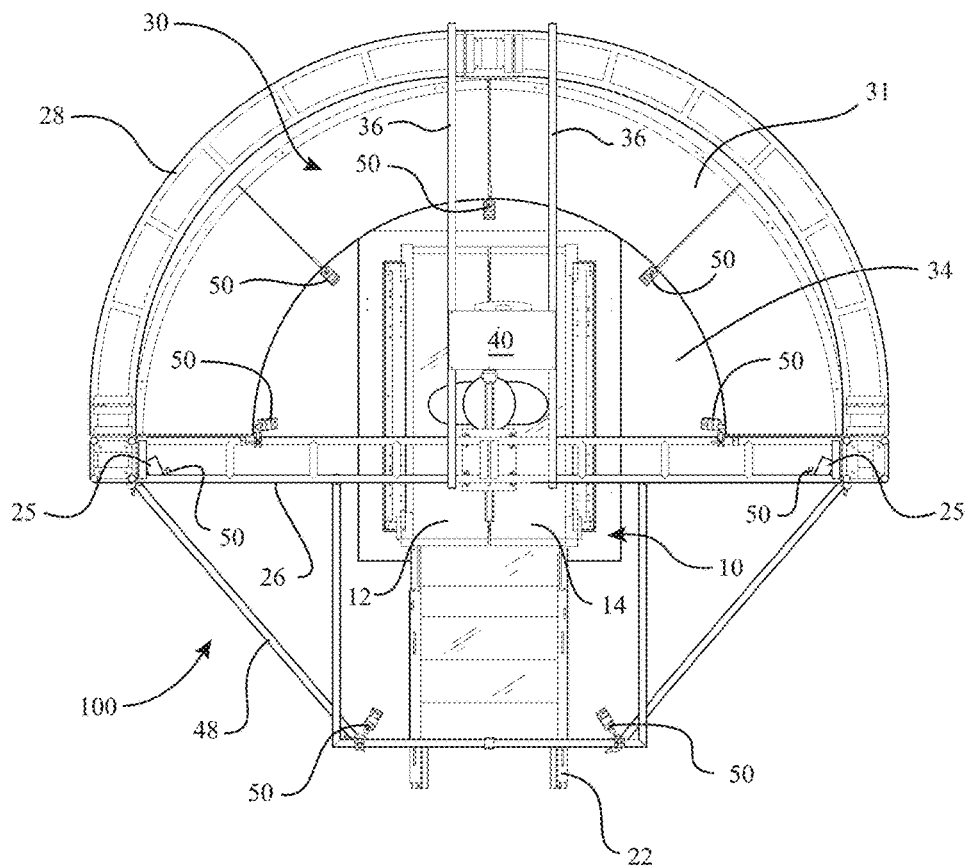
FIG. 3 is a top view of the force measurement system of FIG. 1.

Referring collectively to FIGS. 1-4, it can be seen that, in the illustrative embodiment, the concave projection screen 31 may be supported from a floor surface using a screen support structure formed using a plurality of truss members 24, 26, 28. As shown in FIGS. 1, 2, and 4, the screen support structure 24, 26, 28 is used to elevate the projection screen 31 a predetermined distance above the floor of a room. With continued reference to FIGS. 1, 2, and 4, it can be seen that the illustrated screen support structure comprises a plurality of generally vertical truss members 24 (i.e., three (3) generally vertical truss members 24) that support a plurality of generally horizontal truss members 26, 28 (i.e., two (2) generally horizontal truss members 26, 28), which are disposed at the top of the projection screen 31. As best shown in FIGS. 1 and 3 of the illustrated embodiment, the plurality of generally horizontal truss members 26, 28 include a first linear truss member 26 disposed in the front of the projection screen 31, and a second semi-circular truss member 28 disposed around the curved back side of the projection screen 31. In particular, the two (2) front vertical truss members 24 are securely attached to the peripheral flange 33 of the concave projection screen 31 (e.g., by using a plurality of fasteners and brackets on each side of the flange 33). Because the screen support structure 24, 26, 28 is mostly attached to the upper portion (e.g., upper half) of the screen 31, the screen 31 is generally supported above its center-of-gravity, which advantageously results in a screen mounting arrangement with high structural stability. As shown in FIGS. 1 and 2, one of the plurality of lower leg members 38 are disposed on each of the opposed lateral sides of the screen 31. Also, each of the lower leg members 38 may be provided with a height-adjustable foot for adjusting the height of the screen 31 relative to the floor. Also, as shown in FIGS. 1 and 3, the projector 40 is supported above the screen 31 by a pair of spaced-apart projector support rails 36, each of which is secured directly to the first linear truss member 26 and the second semi-circular truss member 28 of the screen support structure 24, 26, 28, and not directly to the screen 31, so as to minimize the transmission of vibrations from the projector 40 to the hemispherical projection screen 31. Advantageously, the mounting arrangement of the projector 40 on the spaced-apart projector support rails 36 affords adjustability of the projector 40 in a front-to-back direction. It is highly desirable for the hemispherical projection screen 31 to be maintained in a stationary position essentially free from external vibrations so that the subject is completely immersed in the virtual environment being created within the hemispherical projection screen 31. Advantageously, the structural rigidity afforded by the screen support structure 24, 26, 28 of FIGS. 1-4 virtually eliminates the transmission of vibrations to the projection screen 31, including those vibrations emanating from the building itself in which the force measurement system 100 is located. In particular, the screen support structure 24, 26, 28 is designed to minimize any low frequency vibrations that are transmitted to the screen 31.

In the illustrative embodiment, as best shown in the top view of FIG. 3, the top surfaces 16, 18 of the treadmill belts 12, 14 are horizontally spaced apart from the screen support structure 24, 26, 28. In other words, there is a gap horizontally separating the instrumented treadmill 10 from the hemispherical projection screen 31 and its associated screen support structure 24, 26, 28.

As shown in the illustrative embodiment of FIGS. 1-4, the force measurement system 100 may be additionally provided with a motion capture system comprising a plurality of cameras 50. Initially, referring to FIG. 1, it can be seen that a plurality of cameras 50 are disposed around the instrumented treadmill 10 so that the cameras 50 at least partially surround subject disposed on the treadmill 10. In the illustrative embodiment, the cameras 50 are used to track positions of a plurality of markers disposed on a subject as the subject moves his or her torso and limbs in 3-dimensional space. The markers on the subject are used to record the position of the torso and limbs of the subject in 3-dimensional space.

In the illustrative embodiment, with reference to FIGS. 1 and 3, it can be seen that a first plurality of cameras 50 are circumferentially spaced apart around the top cutout 34 in the concave projection screen 31 (i.e., the first plurality of cameras 50 are structurally attached in a load bearing manner around the top cutout 34 of the concave projection screen 31). For example, as best shown in the top view of FIG. 3, the cameras 50 may be generally equally spaced apart about the circumference of the top screen cutout 34. While five (5) cameras 50 are depicted around the circumference of the top screen cutout 34 in the illustrative embodiment, one of ordinary skill in the art will appreciate that more or less cameras may be utilized, provided that the motion of the subject is capable of being captured from substantially all angles. Turning to FIGS. 1 and 2, it can be seen that a second plurality of cameras 50 are spaced apart in front of the instrumented treadmill 10 (i.e., on the open front side of the projection screen 31). In particular, as shown in the illustrative embodiment of FIG. 2, one (1) camera 50 is disposed on each of the generally vertical truss members 24 near the approximate middle of the truss member 24 (i.e., each camera 50 is structurally attached to a respective vertical truss members 24 in a load bearing manner approximately mid-height on the truss member 24). Two (2) additional cameras 50 are attached to the camera mounting structure 48 that extends outwardly from the truss members 24, 26 (i.e., the two additional cameras 50 are structurally attached to the camera mounting structure 48 in a load bearing manner). With combined reference to FIGS. 1 and 2, it can be seen that the camera mounting structure 48 is attached to each of the vertical truss members 24 and the generally linear truss member 26. The camera mounting structure 48 enables the two (2) additional front cameras 50 to be spaced significantly in front of the cameras 50 that are mounted to the respective vertical truss members 24 so that the movements of the subject may be better captured by the motion capture system. While a total of nine (9) cameras 50 are depicted in the illustrative embodiment of FIGS. 1-4, one of ordinary skill in the art will appreciate that more or less cameras can be utilized, provided that the motion of the subject is capable of being captured from substantially all angles.

In the illustrative embodiment, the cameras 50 depicted in FIGS. 1-4 may be in the form of infrared-type (IR) or near infrared-type (NIR) cameras having an angular field of view range between approximately 40 degrees and approximately 80 degrees (or between 40 degrees and 80 degrees). More particularly, in one or more embodiments, the angular field of view range of the cameras 50 may be between approximately 50 degrees and approximately 70 degrees (or between 50 degrees and 70 degrees). Also, in one or more exemplary embodiments, the cameras 50 depicted in FIGS. 1-4 may have a resolution of approximately 1.0 Megapixels, a maximum frame rate of approximately 250 feet per second (fps), and a 4 millimeter to 12 millimeter (4-12 mm) zoom lens. The cameras 50 are positioned in the force measurement system 100 of FIGS. 1-4 so that each marker disposed on a subject standing on the instrumented treadmill 10 is captured by at least two (2) of the cameras 50, and preferably, three (3) of the cameras 50.

In one embodiment of the invention, a subject has a plurality of single reflective markers applied to anatomical landmarks (e.g., the iliac spines of the pelvis, the malleoli of the ankle, and the condyles of the knee), and/or clusters of markers applied to the middle of body segments. As the subject executes particular movements on the instrumented treadmill 10, the data acquisition/data processing device 60 is specially programmed to calculate the trajectory of each reflective marker in three (3) dimensions using the position of the marker captured by the cameras 50. Then, once the positional data is obtained using the motion capture system of FIGS. 1-4, inverse kinematics may be employed in order to further determine the joint angles of the subject. That is, the motion capture system of FIGS. 1-4 generates motion capture data that is representative of the captured motion of the body portions of the subject, and the data acquisition/data processing device 60 is specially programmed to determine the position of the body of the subject (i.e., limbs, torso, head, etc.) and the joint angles of the subject from the motion capture data generated by the motion capture system.

While the motion capture system of FIGS. 1-4 described above employs a plurality of reflective markers, it is to be understood that the invention is not so limited. Rather, in another embodiment of the invention, a markerless motion detection/motion capture system is utilized. The markerless motion capture system uses a plurality of high speed video cameras to record the motion of a subject without requiring any markers to be placed on the subject. Also, while the illustrative embodiment utilizes a plurality of infrared-type (IR) or near infrared-type (NIR) cameras 50, it is to be understood that a non-infrared, optical-based motion detection/motion capture system may alternatively be used. For example, in one alternative embodiment, the optical motion capture system utilizes visible light, rather than infrared light. In addition, an alternative motion capture system may utilize an infrared (IR) emitter to project a plurality of dots onto objects in a particular space as part of a markerless motion capture system. For example, in these one or more alternative embodiments, the markerless motion capture system may comprise a motion capture device with one or more cameras, one or more infrared (IR) depth sensors, and one or more microphones, which may be used to provide full-body three-dimensional (3D) motion capture, facial recognition, and voice recognition capabilities. It is also to be understood that, rather than using an optical motion detection/capture system, a suitable magnetic or electromechanical motion detection/capture system may also be employed to determine the position and joint angles of the subject on the instrumented treadmill 10.

Figure 5:
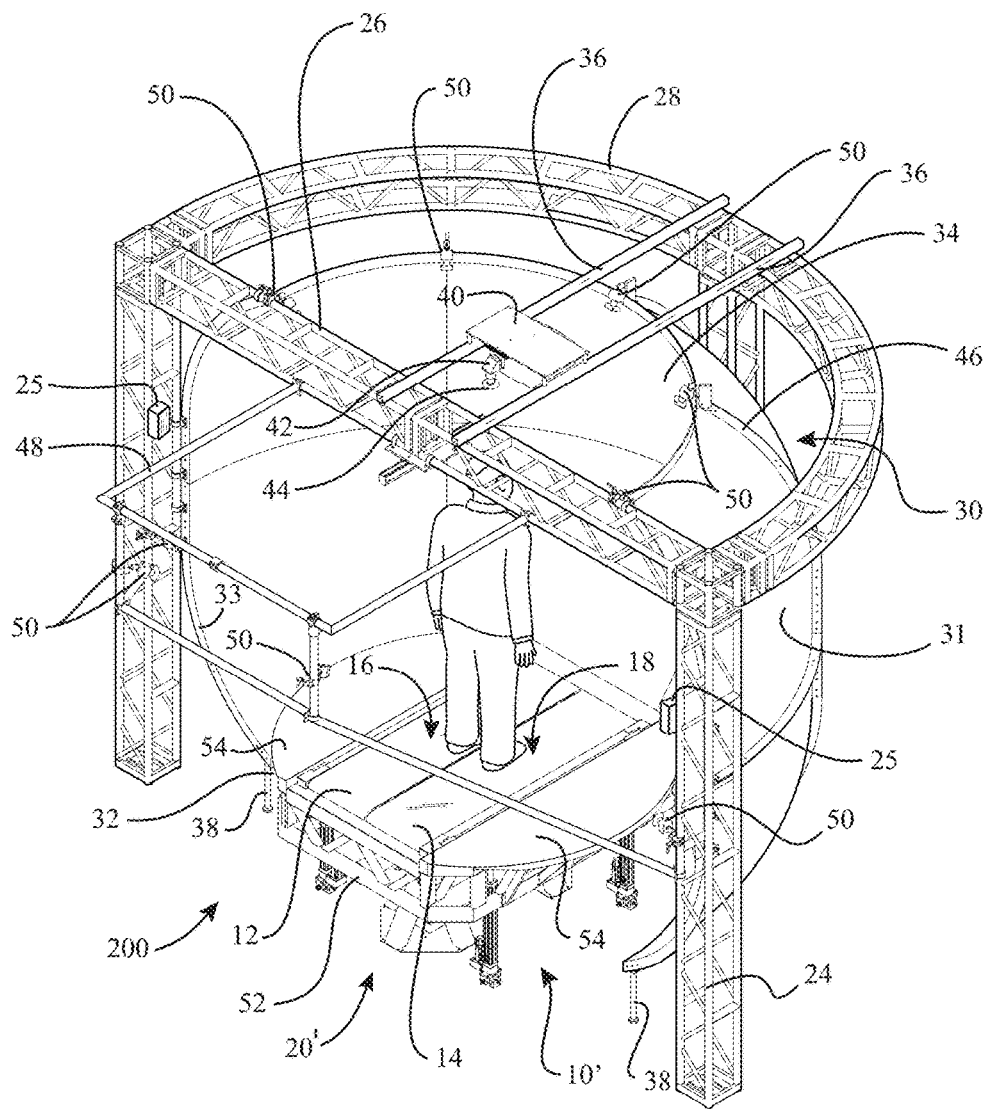
FIG. 5 is a perspective view of a force measurement system with a force measurement assembly in the form of an instrumented treadmill, according to a second embodiment of the invention.

A second embodiment of the force measurement system is seen generally at 200 in FIGS. 5 and 6. With reference to these figures, it can be seen that the force measurement system 200 is similar in most respects to the force measurement system 100 of the first embodiment described above. However, unlike the aforedescribed force measurement system 100, the instrumented treadmill 10' is mounted to the top of a motion base subassembly 20', rather than to the static base subassembly 20 of the first embodiment. As shown in FIGS. 5 and 6, the motion base subassembly 20' comprises a motion base 52 that is capable of displacing the instrumented treadmill 10' in a plurality of different directions. In the illustrated embodiment, the motion base 52 is in the form of a two (2) degree-of-freedom motion base. However, in one or more other embodiments, the motion base 52 may be a six (6) degree-of-freedom motion base that is capable of both translating and rotating the instrumented treadmill 10, 10' in 3-dimensional space (i.e., translating and rotating the instrumented treadmill 10, 10' in all three (3) coordinate directions). Referring again to the second embodiment of FIGS. 5 and 6, it can be seen that the instrumented treadmill 10' is disposed in the middle of a treadmill platform 54. The treadmill platform 54, which is disposed on both sides of the instrumented treadmill 10', makes it easier for the subject to get on and off of the instrumented treadmill 10' during testing.

Figure 10:
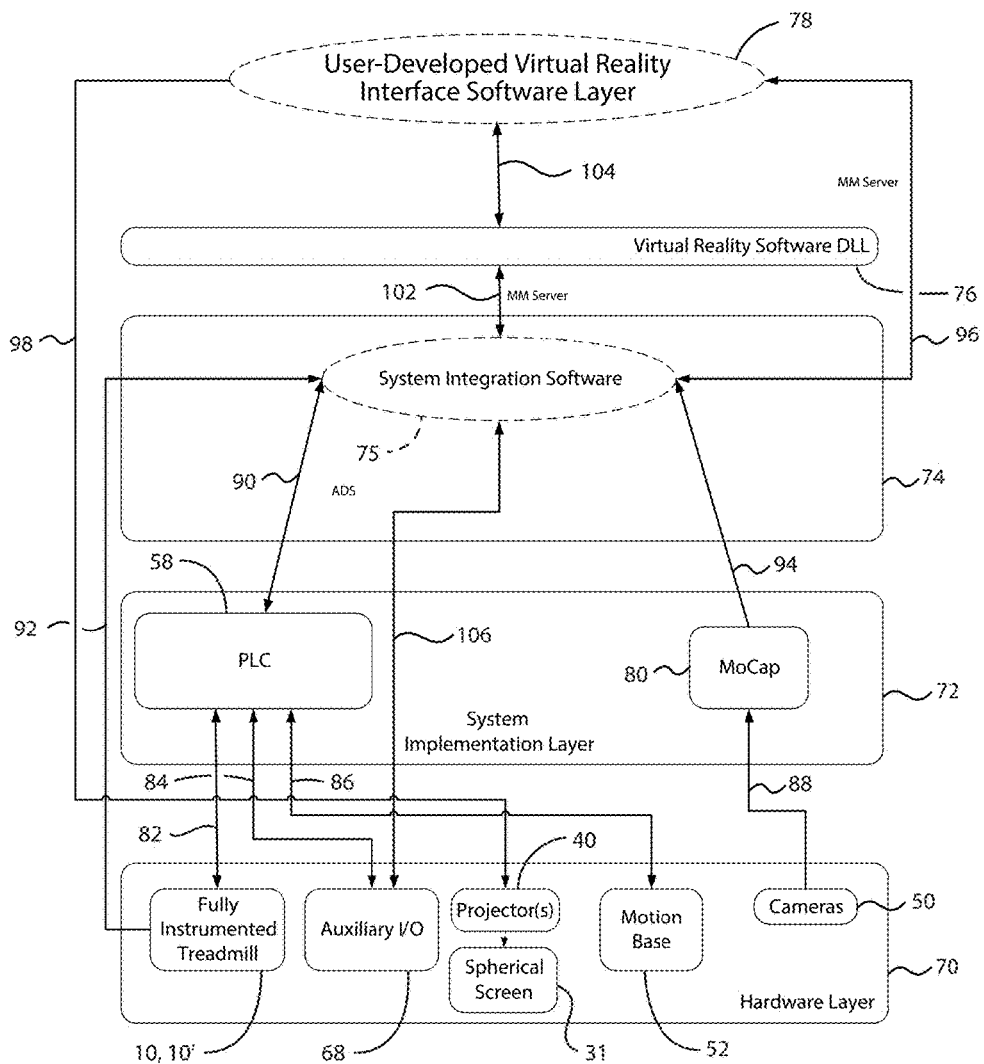
FIG. 10 is a block diagram of the software and hardware architecture of the force measurement system with the force measurement assembly in the form of the instrumented treadmill.

With reference to the block diagram of FIG. 10, the hardware and software architecture of the illustrative embodiments of the force measurement systems 100, 200 will be described in detail. As shown in FIG. 10, the force measurement systems 100, 200 generally include a hardware layer 70, a system implementation layer 72, a system integration software layer 74, a virtual reality dynamic-link library (DLL) software layer 76, and a user-developed virtual reality interface software layer 78 (or user-developed application software layer 78). Each of these hardware and software layers 70, 72, 74, 76, 78 will be described in detail hereinafter, along with the data transfer paths 82-98, 102, and 104 between these layers 70, 72, 74, 76, 78. In the illustrative embodiment, hardwired connections may form the data transfer paths 82-98, 102, and 104 between the constituent components of the force measurement systems 100, 200. Alternatively, data may be transferred wirelessly between the components of the force measurement systems 100, 200 depicted in FIG. 10.

Throughout the present disclosure, when a reference is made to a data acquisition/data processing device 60 or computing device that is "configured to", "arranged to" and/or "configured and arranged to" perform a specific function (e.g., a data acquisition/data processing device 60 configured and arranged to perform a specific function), it is to be understood that, in one or more embodiments of the invention, this means that the data acquisition/data processing device or computing device is specially programmed to carry out the particular function (e.g., the data acquisition/data processing device 60 being specially programmed to perform a specific function).

Initially, referring to FIG. 10, it can be seen that the hardware layer 70 of the force measurement systems 100, 200 includes the instrumented treadmill 10, 10', the spherical screen 31 and projector 40 of the visual display device, the cameras 50 of the motion capture system, the motion base 52 on which the instrumented treadmill 10' of the second embodiment is mounted, and any auxiliary input/output devices 68. For example, as mentioned above, the force measurement systems 100, 200 may include auxiliary input/output devices 68, such as an eye movement tracking system (e.g., as described by U.S. Pat. Nos. 6,113,237 and 6,152,564, which are incorporated by reference in their entireties herein). In addition, as also mentioned above, the auxiliary input/output devices 68 of the systems 100, 200 may include a head movement tracking system comprising one or more accelerometers for measuring the head position and/or velocity of the subject. Also, the auxiliary input/output devices 68 of the systems 100, 200 may further include one or more devices to measure the speed of the treadmill belts and one or more inertial measurement units (IMUs) for measuring the movement of the subject disposed on the instrumented treadmill 10, 10'. The auxiliary input/output devices 68 of the systems 100, 200 may also include a galvanic stimulator that sends an electrical signal to a portion of the body of the subject, one or more treadmill belt tachometers that measure the treadmill belt rotational speed directly, and/or a hand trigger connected to the analog-to-digital (A/D) board.

Next, with reference again to FIG. 10, the system implementation layer 72, the system integration software layer 74, the virtual reality dynamic-link library (DLL) software layer 76, and the user-developed virtual reality interface software layer 78 of the force measurement systems 100, 200 will be described. As shown in FIG. 10, the system implementation layer 72 includes the programmable logic controller (PLC) 58 and motion capture (MoCap) software 80. The functionality of the programmable logic controller 58 was described above. In the illustrative embodiment, which employs a marker-based motion capture system, the motion capture (MoCap) software 80 is used to analyze the reflective markers attached to the subject. The motion capture (MoCap) software 80 may also utilize analog/digital data from the instrumented treadmill 10, 10' to calculate joint kinematics and kinetics and identify gait events, such as heel strike. The system integration software layer 74 comprises the software 75 that synchronizes data from the instrumented treadmill 10, 10' and the camera data processed by the motion capture software 80. The system integration software 75 has the capability to connect any auxiliary input/output devices 68, such as foot switches, EMG devices, galvanic stimulators, inertial measurement units (IMUs), and head/eye trackers through an analog-to-digital (A/D) board. All of this data is synchronized in real-time to process and display information, such as joint kinematics and kinetics, ground reaction forces, spatiotemporal parameters of gait, muscle activation, and rigid body positions. Gait events, such as heel strike and toe-off can be identified. The software also provides real-time biofeedback in terms of visual and/or auditory feedback. Visual feedback is through communication with the user-developed virtual reality interface software layer 78 (or the user-developed application software 78). The auditory feedback comprises one or more speakers provided as part of the force measurement system 100, 200. For example, as shown in the illustrative embodiment of FIG. 1, speakers 25 may be provided on the vertical truss members 24. The speakers 25 are operatively coupled to the data acquisition/data processing device 60 so as to be capable of providing auditory feedback described hereinafter. In the illustrative embodiment, a target may be set up for one gait parameter, such as knee flexion angle, and once that target is reached, an auditory or visual feedback is given to the subject. The virtual reality dynamic-link library (DLL) software layer 76 comprises a plurality of executable files that allows the various programs of the force measurement systems 100, 200 to share code and other resources necessary to perform the particular tasks of the systems 100, 200 (e.g., virtual reality tasks, etc.). In the illustrative embodiment, the virtual reality dynamic-link library (DLL) software layer 76 is visible to the system user of the force measurement system 100, 200. The system architecture layers below the virtual reality DLL software layer 76 (e.g., system implementation layer 72 and the system integration layer 74) are hidden from the system user so as to protect the system data stored in these layers 72, 74 from being inadvertently modified by the system user. In the illustrative embodiment, the virtual reality DLL software layer 76 is in the form of an executable/graphical user interface (GUI)/example software code that lists the variables that the user is able to use to design or modify using the visual interface. The virtual reality DLL software layer 76 also lists the variable names that can be accessed from the system integration software 75, which includes data from the instrumented treadmill 10, 10' and the motion capture (MoCap) software 80. The user-developed virtual reality interface software layer 78 (or user-developed application software layer 78) is responsible for the visual stimulus feedback. The user-developed application software 78 allows the system user to program the visual scenes that provide feedback to the subject (e.g., the closed loop biofeedback described hereinafter). These visual scenes may be standalone, open loop feedback or closed loop feedback. An example of a standalone visual scene is just projecting an animation with no communication between the system integration software/treadmill/cameras and the visual scene itself. With open loop feedback, the data from the system integration software 75 is passed to the visual scene and the visual stimulus is synchronized with either the instrumented treadmill 10, 10' or the cameras 50. In the illustrative embodiment, the treadmill belt speed and the speed scale factor is sent to the user-developed application software 78 which, in turn, uses these parameters to set the speed of the optic flow. Thus, the optic flow is able to be synchronized with the treadmill belt speed. As another example, a pelvic marker position may be sent to the user-developed application software 78 so that the optic flow may be synchronized with the pelvic marker instead. The ground reaction forces and the center-of-pressure (COP) determined using the instrumented treadmill 10, 10' are also sent to the user-developed application software 78 so that the visual scene is capable of being changed based on the ground reaction forces and/or the center-of-pressure of the subject. In the illustrative embodiment, different levels of difficulty are capable of being set up in the visual scene based on the subject performance. The subject performance may be quantified based on the treadmill or camera data. For example, the ground reaction force during heel strike or the position of some joint. The closed loop feedback functionality of the force measurement systems 100, 200 will be described in detail hereinafter. As one example of closed loop feedback carried out by the system 100, 200, the belt speed of the instrumented treadmill 10, 10' changes in accordance with the visual scene on the spherical screen 31 of the visual display device 30.

In one or more embodiments, the force measurement systems 100, 200 may each comprise two (2) data acquisition/data processing devices (i.e., two (2) computers) for executing the software described above. The first computer has the treadmill control software, the motion capture software 80, and the system integration software 75 loaded thereon. The second computer has the virtual reality software 76 and the user-developed application software 78 loaded thereon. In one or more alternative embodiments, the force measurement systems 100, 200 may each comprise a single data acquisition/data processing device 60 (i.e., a single computer) for executing the software described above. In these one or more alternative embodiments, the data acquisition/data processing device 60 may have the treadmill control software, the motion capture software 80, the system integration software 75, the virtual reality software 76, and the user-developed application software 78 all loaded thereon.

Figure 11:
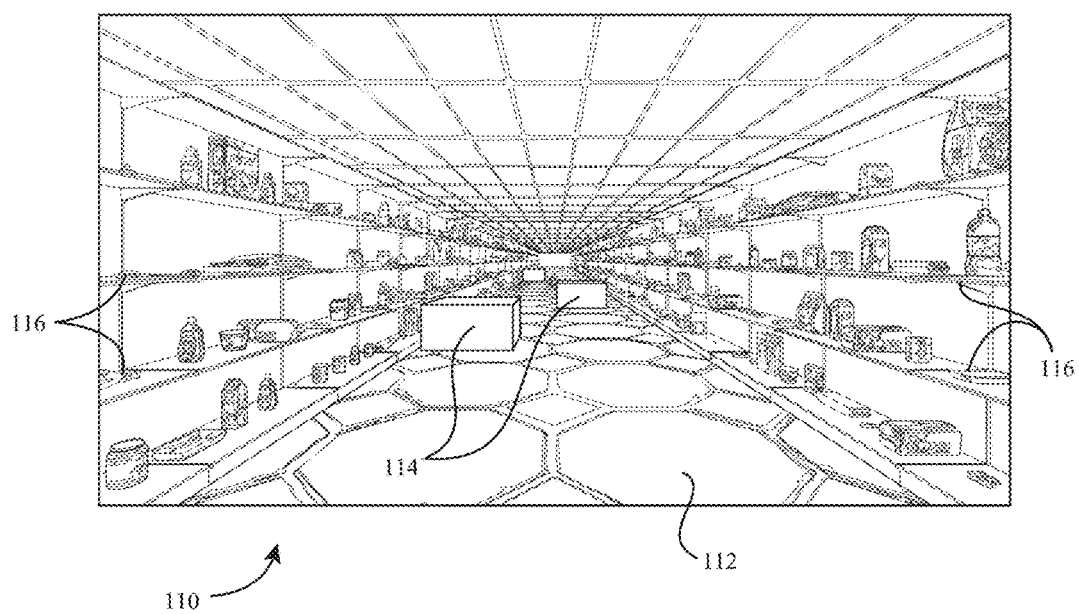
FIG. 11 is a screen image of an immersive grocery aisle scene displayed on the output screen of the visual display device of the force measurement system, according to an embodiment of the invention.
Figure 12:
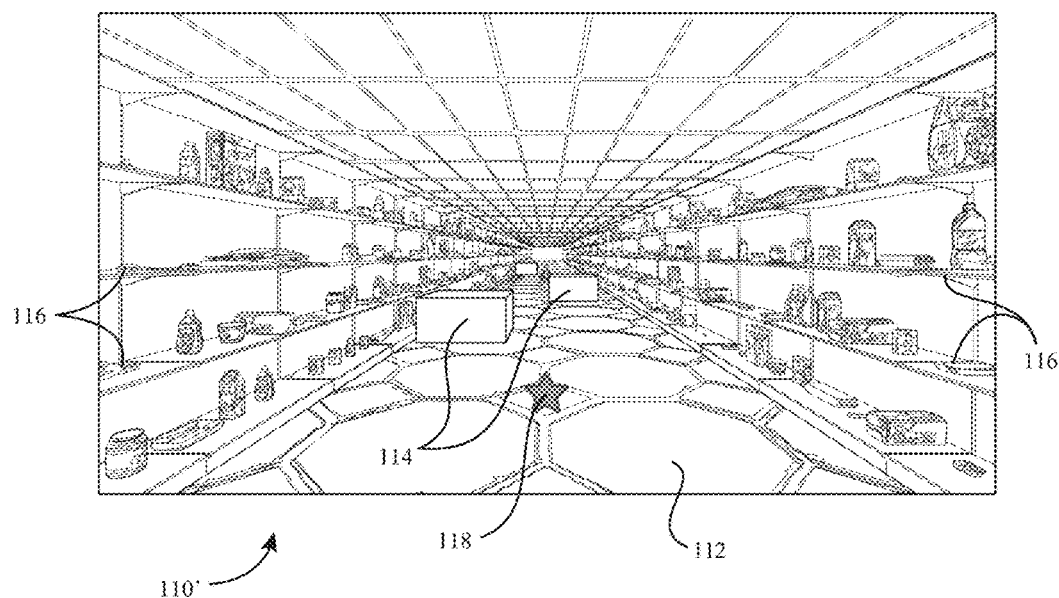
FIG. 12 is another screen image of the immersive grocery aisle scene of FIG. 11.
Figure 13:
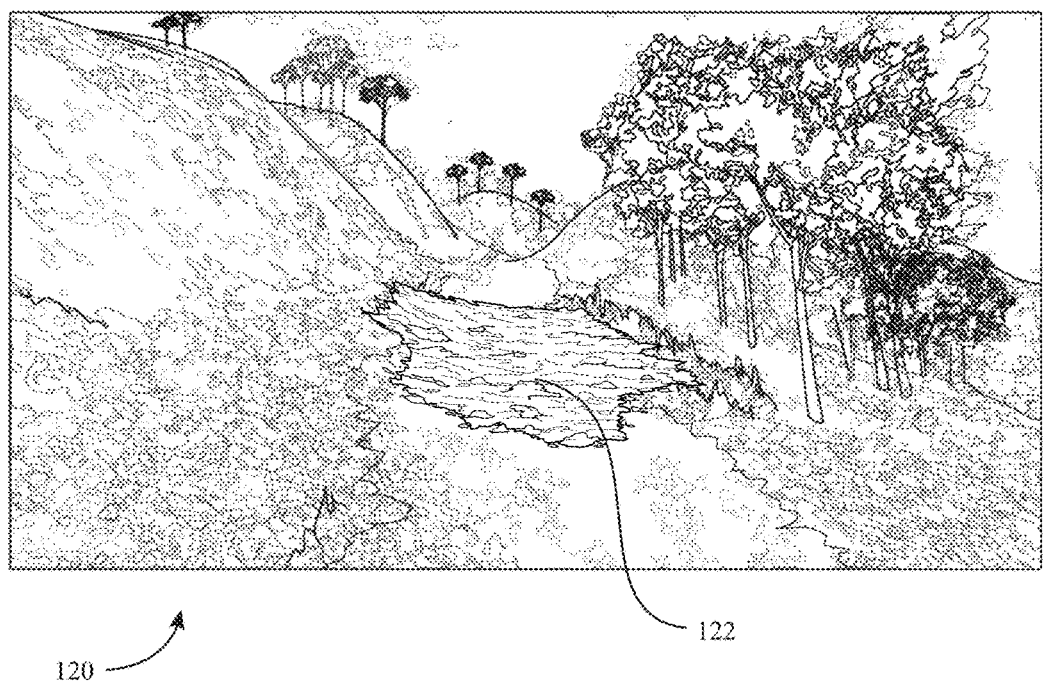
FIG. 13 is a screen image of an immersive island pathway scene displayed on the output screen of the visual display device of the force measurement system, according to another embodiment of the invention, wherein a first type of pathway ground surface is illustrated.
Figure 14:
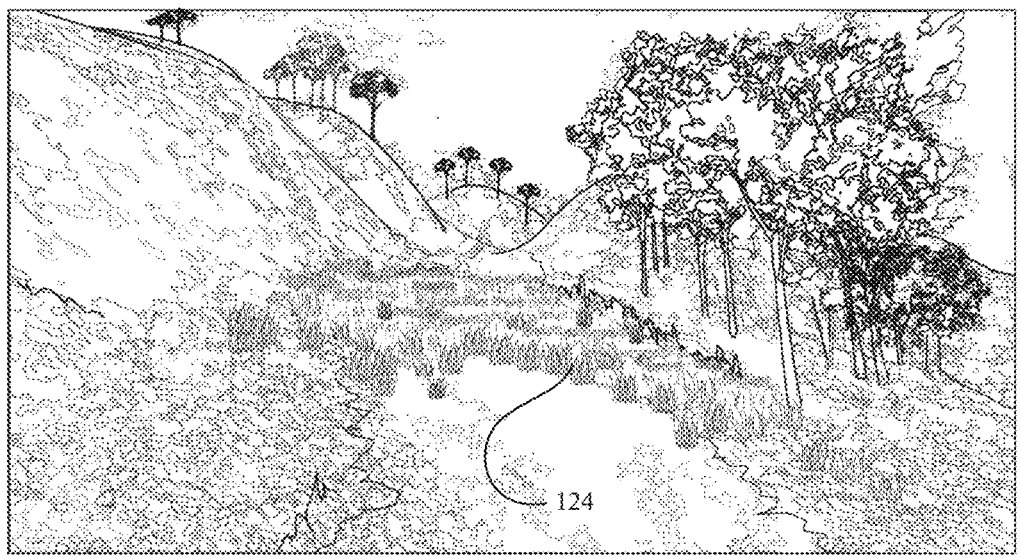
FIG. 14 is another screen image of the immersive island pathway scene of FIG. 13, wherein a second type of pathway ground surface is illustrated.
Figure 15:
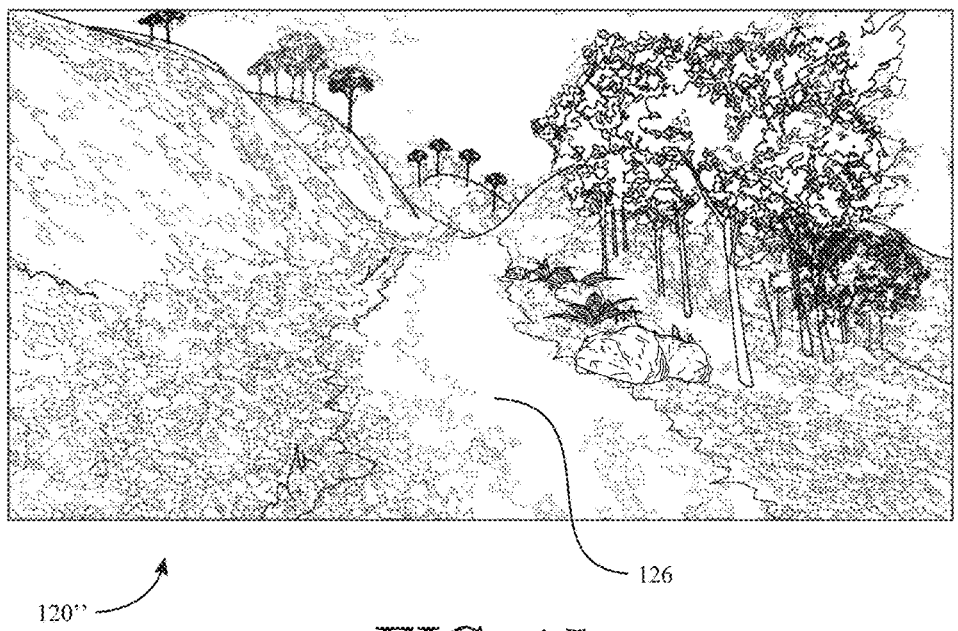
FIG. 15 is yet another screen image of the immersive island pathway scene of FIG. 13, wherein a third type of pathway ground surface is illustrated.
Figure 16:
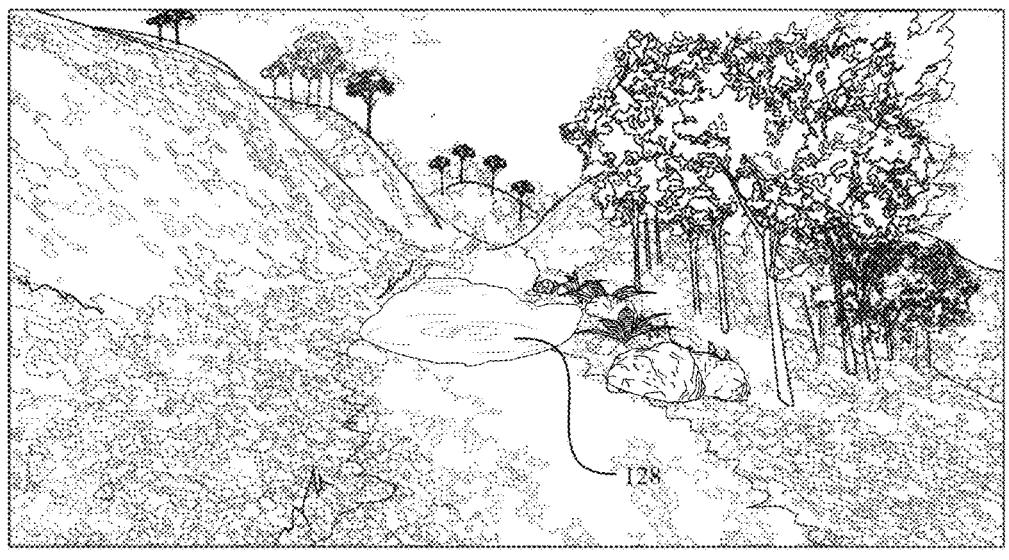
FIG. 16 is yet another screen image of the immersive island pathway scene of FIG. 13, wherein a portion of the pathway has a puddle of water disposed thereon.
Figure 17:
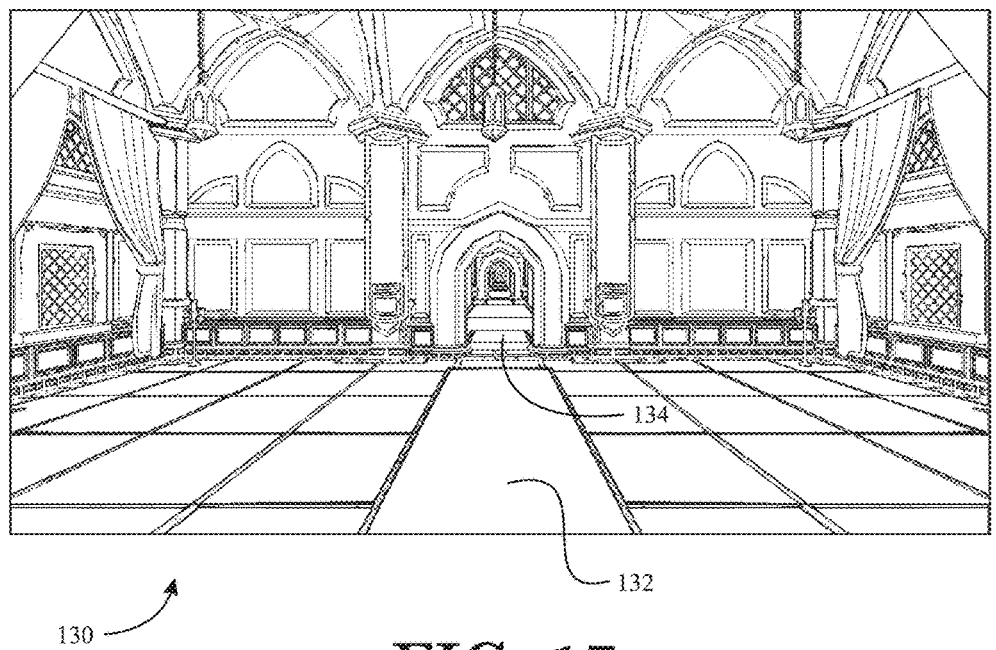
FIG. 17 is a screen image of an immersive castle scene displayed on the output screen of the visual display device of the force measurement system, according to yet another embodiment of the invention.

In the illustrative embodiment, the force measurement systems 100, 200 are capable of providing both explicit motor training and implicit motor training for the subject. When explicit motor training is provided, the scene displayed on the spherical screen 31 of the visual display device 30 merely graphically depicts the movement of the subject so as to provide feedback to the subject. For example, in the case of explicit feedback, the height of the subject's foot from the surface level and/or the joint kinematics of the subject may be displayed on the spherical screen 31 of the visual display device 30. Although, when implicit motor training is provided, the subject is in control of the feedback that is provided on the spherical screen 31 of the visual display device 30. For example, in the case of implicit feedback, when a subject is progressing down a virtual grocery store aisle on the spherical screen 31 of the visual display device 30 (e.g., as shown in FIGS. 11 and 12), the number of obstacles 114 avoided by the subject, and the number of obstacles 114 that the subject collides with may be recorded by the data acquisition/data processing device 60 of the system 100, 200. The data acquisition/data processing device 60 of the system 100, 200 may also be specially programmed to display the recorded obstacle avoidance and obstacle collision quantities on the spherical screen 31 of the visual display device 30 in order to provided implicit feedback to the subject undergoing the training or testing on the instrumented treadmill 10, 10'.

With reference to FIGS. 11-12, an immersive grocery aisle scene in accordance with one illustrative embodiment of the invention will be described. Initially, with reference to FIG. 11, it can be seen that the grocery aisle screen image 110 comprises a grocery aisle 112 bounded by a plurality of shelves 116 disposed on each of the opposite sides of the grocery aisle 112. A plurality of obstacles (e.g., boxes 114) is disposed in the grocery aisle 112 so that the subject is required to maneuver around the obstacles 114 in an effort to avoid colliding with one of the obstacles 114. The grocery aisle screen image 110' of FIG. 12 is identical to the grocery screen image 110 of FIG. 11, except that the screen image 110' comprises a star 118 disposed in the screen image 110'. The star 118 represents the position of the subject in the screen image 110'. In one or more alternative embodiments, the star 118 may be replaced with an avatar or a silhouette of the subject in the screen image 110'. In the immersive grocery aisle scenario of FIGS. 11 and 12, the data acquisition/data processing device 60 may be specially programmed to control the movement of the star 118 on the screen in accordance with the center of pressure (COP) determined by the instrumented treadmill 10, 10'. For example, when a subject leans to the left on the instrumented treadmill 10, 10', the star 118 in the immersive grocery aisle scene is displaced to the left. Conversely, when a subject leans to the right on the instrumented treadmill 10, 10', the star 118 in the immersive grocery aisle scene is displaced to the right. In this manner, the subject is able to avoid colliding with the obstacles 114 in the immersive grocery aisle scene by appropriately shift his or her weight to the right or to the left, thereby moving the star 118 to a side of the obstacle 114. In the immersive grocery aisle scenario of FIGS. 11 and 12, when a subject collides with one of the obstacles 114 in the scene (i.e., when the star 118 representing the subject collides with one of the obstacles 114), the data acquisition/data processing device 60 may be specially programmed to reduce the treadmill belt speed so as to simulate a collision with the virtual obstacle 114 (i.e., by reducing the speed set point sent to the speed adjustment mechanisms of the treadmill belts). Then, after the subject clears the virtual obstacle 114 (i.e., once the star 118 is shifted to a side of the obstacle 114 by the subject), the data acquisition/data processing device 60 may be specially programmed to increase the treadmill belt speed to its speed prior to the collision with the virtual obstacle 114 so that the subject may continue to progress down the virtual grocery aisle in a normal fashion. Although FIGS. 11 and 12 depict generally planar images, rather than a concave image projected on the spherical screen 31 of the visual display device 30, it is to be understood that the immersive grocery aisle scenario, like the other scenarios described hereinafter, is configured to be implemented on the spherical screen 31 that at least partially surrounds the subject.

In a further embodiment, while walking through the immersive grocery aisle scene of FIGS. 11-12, the subject may be instructed to overcome obstacles 114 by lifting his foot so as to step over the obstacles 114. In this further embodiment, a reflective marker may be attached to the foot of the subject so that the cameras 50 of the motion capture system described above are able to detect the foot position of the subject by means of this reflective marker. If the foot is raised high enough by the subject, the subject clears the obstacle 114. However, if the subject does not raise his or her foot to the desired height so as to clear the obstacle 114, the data acquisition/data processing device 60 may be programmed to generate a red line on the scene which indicates the additional height the foot has to reach. In one or more embodiments, the data acquisition/data processing device 60 may be programmed to compute an error term by subtracting the actual foot height achieved by the subject from the height of the obstacle 114 (i.e., Obstacle Height−Foot Height From Marker=Error). In these embodiments, the acquisition/data processing device 60 determines the height of the red line in the scene by adding the error term to the actual foot height achieved by the subject. In one or more other embodiments, the data acquisition/data processing device 60 may be programmed to compute an augmented error term by multiplying the aforedescribed error term by a numerical factor (e.g., 1.25, 1.5, 2.0, etc.). In these embodiments, the acquisition/data processing device 60 determines the height of the red line in the scene by adding the augmented error term to the actual foot height achieved by the subject. As such, the error term may be difference between the desired and current foot position, or in case of augmented error, the error term may be multiplied by a numerical factor.

Now, referring again to FIG. 10, the data transfer paths 82-98, 102, and 104 between the hardware and software layers 70, 72, 74, 76, 78 of the force measurement systems 100, 200 will be explained. In FIG. 10, it can be seen that the instrumented treadmill 10, 10' is operatively coupled to the programmable logic controller (PLC) 58 by the data transfer path 82, which allows data to be transferred in both directions between the instrumented treadmill 10, 10' and the programmable logic controller (PLC) 58. For example, the treadmill control signals are sent from the programmable logic controller (PLC) 58 to the instrumented treadmill 10, 10', and feedback data in the form of belt speed, acceleration, and position is sent from the instrumented treadmill 10, 10' to the programmable logic controller (PLC) 58. Also, as shown in FIG. 10, the auxiliary input/output devices 68 are operatively coupled to the programmable logic controller (PLC) 58 by the data transfer path 84, which allows data to be transferred in both directions between the auxiliary input/output devices 68 and the programmable logic controller (PLC) 58. For example, as described above, the auxiliary input/output devices 68 of the system 100, 200 may be connected to the input/output (I/O) module of the programmable logic controller 58, which enables the auxiliary input/output devices 68 to be easily synchronized with the rest of the system components (e.g., if one or more treadmill belt tachometers are provided as auxiliary input/output devices 68, it is advantageous to connect these devices to the PLC 58 so that they are synchronized with the operation of the instrumented treadmill 10, 10'). Further, as illustrated in FIG. 10, it can be seen that the motion base 52 is operatively coupled to the programmable logic controller (PLC) 58 by the data transfer path 86, which allows data to be transferred in both directions between the motion base 52 and the programmable logic controller (PLC) 58. For example, motion base control signals are sent from the programmable logic controller (PLC) 58 to the motion base 52, and feedback data in the form of motion base position, velocity, and acceleration is sent from the motion base 52 to the programmable logic controller (PLC) 58.

Also, as depicted in FIG. 10, it can be seen that data acquired by the cameras 50 of the motion capture system is transferred via the data transfer path 88 to a data acquisition/data processing device (i.e., computing device) with the motion capture software 80 loaded thereon. As described above, the motion capture software 80 is used to calculate joint kinematics and kinetics using the data from the instrumented treadmill 10, 10' and the motion capture system, and to identify gait events, such as heel strike. Referring again to FIG. 10, it can be seen that data is sent from the programmable logic controller (PLC) 58 to the system integration software 75 via the data transfer path 90. The data path 90 is used to transfer data from the firmware of the PLC 58 to the system integration software 75 so that the variables defined in the firmware are capable of being accessed by the treadmill control software on the computer user interface (UI) of the instrumented treadmill 10, 10' using this protocol. In addition, as shown in FIG. 10, analog force measurement data is sent from the instrumented treadmill 10, 10' to the system integration software 75 via the data transfer path 92. Advantageously, the data paths 82, 90, 92 allow both analog data and digital data to be collected from the instrumented treadmill 10, 10' and to be delivered to the system integration software 75 simultaneously. As described above, the analog force measurement data acquired by the pylon-type force transducers 56 of the instrumented treadmill 10, 10' may be converted to digital force measurement data using an analog-to-digital (A/D) board, and then converted to output load data by means of a data acquisition/data processing device (i.e., measurement computing device). If the researcher or clinician wants to use analog data instead of digital data, the data path 92 enables the system integration software 75 to directly read the analog data from the instrumented treadmill 10, 10'. Also, as illustrated in FIG. 10, data processed by the motion capture software 80 is sent to the system integration software 75 via the data transfer path 94. The data path 94 allows the marker data collected by the cameras 50 to be sent to the system integration software 75 for processing. This marker data is used to calculate the joint kinematics and kinetics, which are synchronized with the force data from the instrumented treadmill 10, 10', so that the movement of the subject is able to be displayed in real time on the spherical screen 31 of the visual display device 30 during a gait trial.

With reference once again to FIG. 10, it can be seen that data is transferred between the system integration software 75 and the user-developed virtual reality interface software layer 78 (or user-developed application software layer 78) via the data transfer path 96. For example, the data is transferred between the system integration software 75 and the user-developed application software layer 78 by means of a motion management (MM) server. The MM server is the two-way communication protocol used for the data transfer between the system integration software 75 and the user-developed application software 78. Any data that is available in the system integration software 75 is capable of being sent to the user-developed application software 78. For example, in the illustrative embodiment, the treadmill belt speed, the speed scaling factor, the calculated output forces, and the center of pressure (COP) is sent to the user-developed application software 78. The belt speed and speed scaling factor are used to control the optic flow at the same speed as the treadmill belts. The output forces and center-of-pressure (COP) may be simply displayed on the spherical screen 31 in graphical form for biofeedback purposes (e.g., feedback display charts), or alternatively, may be used for any complex visual feedback, such as that used in animation. As described hereinafter, in some embodiments, the data transfer path 96 may be omitted when the force measurement systems 100, 200 are provided with a separate virtual reality software dynamic-link library (DLL) layer. As an example, the belt speed of the instrumented treadmill 10, 10' may be transferred from the system integration software 75 to the user-developed application software 78 so that the user-developed application software 78 may use these parameters to set the speed of the optic flow. Conversely, as another example, scene selection data may be transferred from the user-developed application software 78 to the system integration software 75 if there are multiple scenes from which a user is able to choose. In this example, a scene selection command is sent from the user-developed application software 78 to the system integration software 75 so that a user is able to select, for example, different ground surface types in a virtual scenario or different levels of difficulty in a virtual scenario. In the illustrative embodiment, all of the variables in the virtual scenario are stored in the system integration layer 74 (e.g., ground surface type, etc.).

Also, as illustrated in FIG. 10, it can be seen that commands are sent from the user-developed virtual reality interface software layer 78 (or user-developed application software 78) to the projector 40 of the visual display device 30 via the data transfer path 98 so that the scene images generated by the user-developed application software 78 may be displayed on the spherical screen 31 of the visual display device 30. Turning again to FIG. 10, when a separate virtual reality software DLL layer is provided, it can be seen that data is transferred between the system integration software 75 and the virtual reality software DLL 76 via the data transfer path 102. More particularly, as shown in FIG. 10, data is sent from the system integration software 75 to the virtual reality software DLL 76 via the MM server, and from the virtual reality software DLL 76 to the system integration software 75 via the MM server. In FIG. 10, it can also be seen that, when a separate virtual reality software DLL layer is provided, data is transferred between the virtual reality software DLL 76 and the user-developed application software 78 via the data transfer path 104. Like the data path 102 between the system integration software 75 and the virtual reality software DLL 76, the data path 104 between the virtual reality software DLL 76 and the user-developed application software 78 also allows data to be transferred in both directions. When the force measurement systems 100, 200 are provided with the separate virtual reality software DLL layer, the data paths 102, 104 may be used in lieu of the data path 96.

Finally, with reference again to the block diagram of FIG. 10, it can be seen that the system integration software 75 is capable of sending and receiving signals to and from the auxiliary input/output devices 68 via the data transfer path 106. For example, the system integration software 75 may send and receive signals from the head movement tracking system, the treadmill belt speed measurement devices, the one or more inertial measurement units (IMUs), the galvanic stimulator and/or the hand trigger mentioned above. For example, when a hand trigger is provided as one of the auxiliary input/output devices 68 to the system 100, 200, the hand trigger may send a pulse to the system integration software 75, which can be used to mark events in the data set based on the researcher's observations or clinician's observations. Advantageously, the auxiliary input/output devices 68 provide additional information about the movement of the subject, and also may enable various muscles of the subject to be activated (i.e., in the case of galvanic stimulator). For example, the head tracker is capable of determining the position of the subject's head, while the eye tracker is capable of determining the position of the subject's eyes. Also, when the output of these two devices is combined, the gaze direction of the subject is capable of being determined. As another example, when electromyography (EMG) devices are provided as one of the auxiliary input/output devices 68, information about the muscle activations of the subject are capable of being determined by the system 100, 200. As yet another example, when a foot switch is provided as one of the auxiliary input/output devices 68, the foot switch may be used to indicate gait patterns of the subject or to trigger auditory feedback that is delivered to the subject. As still another example, when a galvanic stimulator is provided as one of the auxiliary input/output devices 68, signals may be sent to the galvanic stimulator based on one or more gait events in order to trigger a voltage to activate certain muscles of the subject. Advantageously, because the data transfer path 106 allows auxiliary input/output devices 68 to be connected directly to the system integration software 75, the number of analog inputs to the programmable logic controller (PLC) 58 is able to be reduced as a result of the auxiliary input/output devices 68 not all being required to be connected to the PLC 58.

Next, the closed loop biofeedback functionality of the illustrative force measurement systems 100, 200 will be described with reference to immersive scenarios depicted in FIGS. 13-23. In the illustrative embodiment, the control parameters of the instrumented treadmill 10, 10' may change in accordance with the scene that is being displayed on the spherical screen 31 of the visual display device 30. Also, auditory feedback may be provided to the subject while he or she is disposed on the instrumented treadmill 10, 10'. In addition, the closed loop biofeedback functionality of the system 100, 200 may have varying levels of difficulty. Further, a head movement tracking system to measure the head movement of the subject and/or an eye movement tracking system to measurement the eye movement of the subject may be utilized in conjunction with closed loop biofeedback functionality of the systems 100, 200. Advantageously, the closed loop biofeedback functionality of the illustrative force measurement systems 100, 200 is capable of being used with a diverse selection of subject populations (e.g., adult/pediatric, healthy/pathological, etc.).

In an exemplary embodiment, the data acquisition/data processing device 60 of the force measurement systems 100, 200 generates a scene image with a plurality of different ground surfaces (e.g., concrete, grass, sand, gravel, etc.). These scene images are then displayed on the on the spherical screen 31 of the visual display device 30 so that the scene images are able to viewed by the subject while he walks or runs on the instrumented treadmill 10, 10'. In this exemplary embodiment, the control variable is the treadmill belt speed and the output variable is the number of miles traveled by the subject on the instrumented treadmill 10, 10' (i.e., belt travel).

In the exemplary embodiment, the decreasing order of treadmill belt speed for different ground surfaces may be as follows: (i) paved ground surface—highest belt speed, (ii) grass ground surface—intermediate belt speed, and (iii) sand or dirt ground surface—lowest belt speed. In the user-developed application software 78, the variable "grd_surface" may be associated with the type of ground surface that is being displayed on the spherical screen 31 of the visual display device 30 to the subject. As the ground surface that is displayed on the spherical screen 31 changes, the variable "grd_surface" is continuously updated in the user-developed application software 78, and the values of the variable "grd_surface" are continually passed to the system integration software 75 at the system integration layer 74. By means of communicating with the instrumented treadmill 10, 10' through the programmable logic controller 58, the system integration software 75 then continually updates the treadmill belt speed based on the value of the variable "grd_surface". For example, when the variable "grd_surface" is set to a value "3" indicative of a paved ground surface, the treadmill belt speed may be set to 2.0 meters per second (2.0 m/s). When the variable "grd_surface" is set to a value "2" indicative of a grass ground surface, the treadmill belt speed may be set to 1.5 meters per second (1.5 m/s). Finally, when the variable "grd_surface" is set to a value "1" indicative of a sand ground surface, the treadmill belt speed may be set to 1.0 meters per second (1.0 m/s).

With reference to FIGS. 13-16, an immersive island pathway scene in accordance with another illustrative embodiment of the invention will be described. Initially, with reference to FIG. 13, it can be seen that the island screen image 120 comprises a walking pathway with a rocky portion 122 forming a portion of the pathway. The rocky portion 122 of the island pathway represents a paved ground surface encountered by the subject. When the subject walks across the rocky portion 122 of the pathway in the virtual island scene, the user-developed application software 78, sets the variable "grd_surface" to a value "3" indicative of a paved ground surface, which in turn, results in the treadmill belt speed assuming its highest setting, as described above. Next, turning to FIG. 14, it can be seen that the island screen image 120' comprises a walking pathway with a grassy portion 124 forming a portion of the pathway. When the subject walks across the grassy portion 124 of the pathway in the virtual island scene, the user-developed application software 78, sets the variable "grd_surface" to a value "2" indicative of a grassy ground surface, which in turn, results in the treadmill belt speed assuming its intermediate setting, as described above. Then, with reference to FIG. 15, it can be seen that the island screen image 120" comprises a walking pathway formed from a combination of dirt and sand 126. When the subject walks across the walking pathway comprising the combination of dirt and sand 126 in the virtual island scene, the user-developed application software 78, sets the variable "grd_surface" to a value "1" indicative of a dirt and/or sand ground surface, which in turn, results in the treadmill belt speed assuming its lowest setting, as described above.

As another exemplary scenario in the exemplary embodiment, the subject may be walking along on a paved or other surface type in the virtual environment displayed on the spherical screen 31 of the visual display device 30, and then suddenly encounters a puddle of water on the walking surface. In this exemplary scenario, while the subject is crossing the puddle, the treadmill belt speed is reduced. For example, in the immersive island pathway scene of FIG. 16, the island screen image 120''' comprises a walking pathway with a puddle 128 disposed across a portion of the walking path. When the subject walks across the puddle 128 in the virtual island scene, the treadmill belt speed is reduced. In order to implement this reduction in treadmill belt speed, the user-developed application software 78 may set a Boolean variable "grd_puddle" continuously while the subject navigates through the virtual environment. This variable "grd_puddle" is continually received by the system integration software 75 from the user-developed application software 78. If the variable "grd_puddle" set is set to "0", the treadmill belt speed is set at the current belt speed. However, if a puddle appears in the virtual environment, the variable "grd_puddle" is set to "1", and this value is sent to the system integration software 75. Then, by means of communicating with the instrumented treadmill 10, 10' through the programmable logic controller 58, the system integration software 75 reduces the treadmill belt speed by a predetermined amount (e.g., current treadmill belt speed of 2.0 m/s−0.25 m/s=1.75 m/s). In a similar manner, the current belt speed of the instrumented treadmill 10, 10' may be reduced for an uneven surface or irregular rocky surface in the virtual environment.

As yet another exemplary scenario in the exemplary embodiment, the subject may be instructed to direct his or gaze at targets that will appear on the spherical screen 31 of the visual display device 30 (e.g., the targets 136 in the immersive castle scene of FIGS. 17-23 that will be described hereinafter). In this scenario, the subject may be outfitted with a head tracker and/or an eye tracker in order to indicate the gaze direction of the subject in order to determine whether or not the subject is looking at the intended targets on the screen 31. In addition to, or as an alternative to the head tracker and/or eye tracker, the subject may be provided with a pointing device so that he or she is able to indicate the target direction by pointing to the targets on the screen. In this exemplary scenario, the variables "target_reached" and "target_focus" may be maintained in the user-developed application software 78, with both being set to values of "0" at the beginning of the subject testing or training routine. The values of these variables are sent to the system integration software 75 at the system integration layer 74. When a target appears on the screen 31, the value of the variable "target_reached" is set to "1" in the user-developed application software 78, and the position of the subject's head and/or eyes is determined using the head tracker and/or eye tracker. Similarly, if the pointing device is used in addition to, or as an alternative to the head tracker and/or eye tracker, the pointing direction of the subject is determined. If the subject is determined to be gazing in the direction of the target and/or pointing at the target, the value of the variable "target_focus" is set to "1", otherwise the value of the "target_focus" is set to "0". If both the variable "target_reached" is set to "1" and the variable "target_focus" is set to "1", treadmill belt speed is set to, or remains at the current treadmill belt speed. Although, if the variable "target_reached" is set to "1" and the variable "target_focus" is set to "0", the system integration software 75 reduces the treadmill belt speed by a predetermined amount (e.g., current treadmill belt speed of 2.0 m/s−0.25 m/s=1.75 m/s). That way, the speed of the treadmill belt speed is reduced so as to make it easier for the subject to properly focus on the intended target.

In one or more embodiments, the intended targets that are displayed on the spherical screen 31 of the visual display device 30 are not part of a virtual keyboard on the screen 31 for controlling the operation of the treadmill, wherein the virtual keyboard is intended to replace and/or supplement the typical hardware-based treadmill control panel. Rather, as described hereinafter in the illustrative embodiment of FIGS. 17-23, the intended targets are objects in an immersive scene displayed on the screen 31 of the visual display device 30, such as the targets 136 described below.

Figure 18:
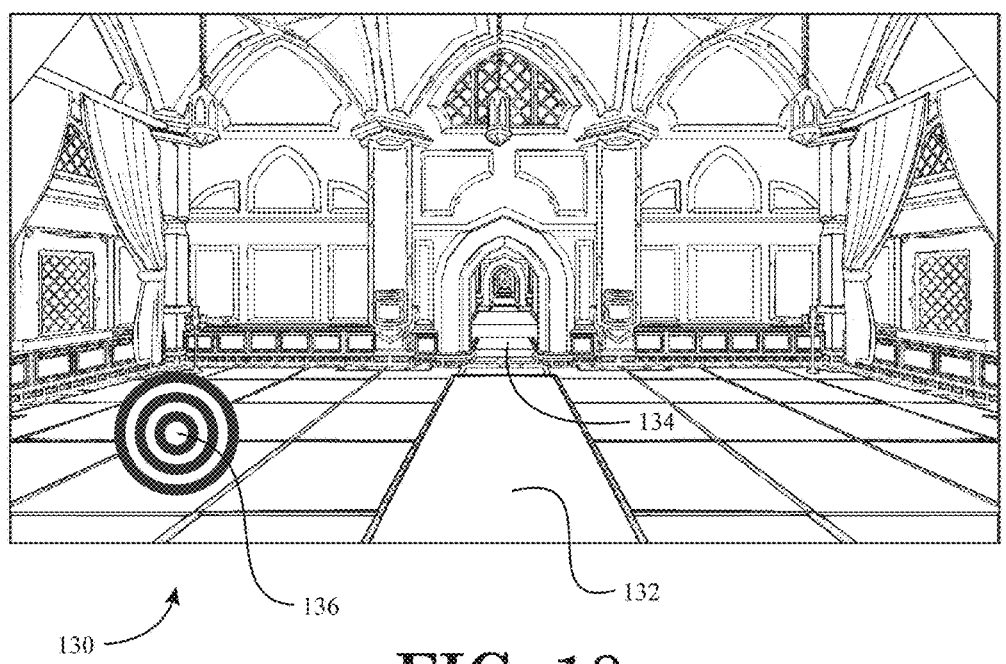
FIG. 18 is another screen image of the immersive castle scene of FIG. 17, wherein a target is provided in the bottom, left-hand corner of the screen.
Figure 19:
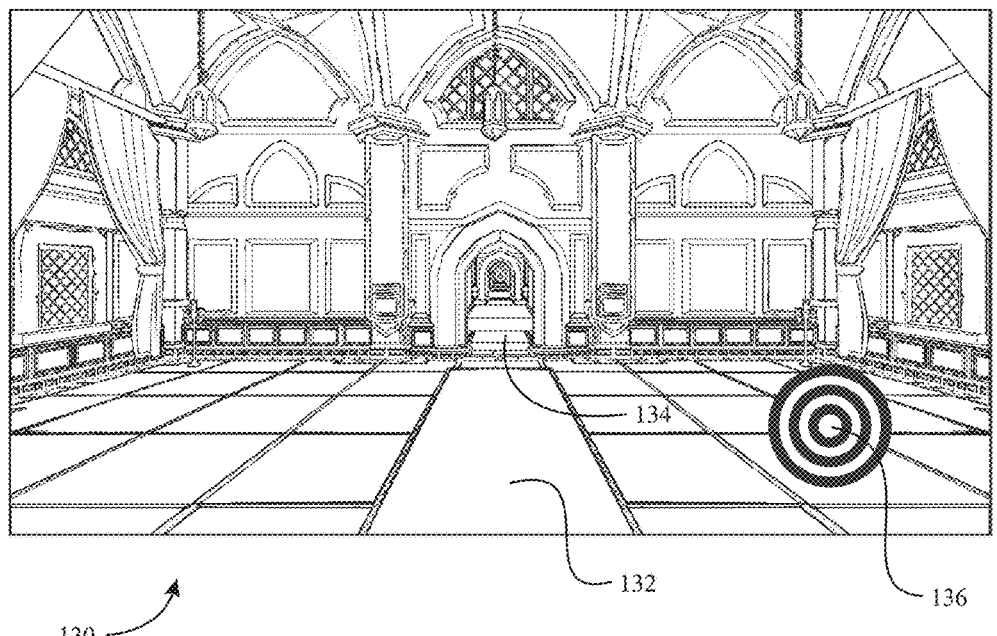
FIG. 19 is yet another screen image of the immersive castle scene of FIG. 17, wherein a target is provided in the bottom, right-hand corner of the screen.
Figure 20:
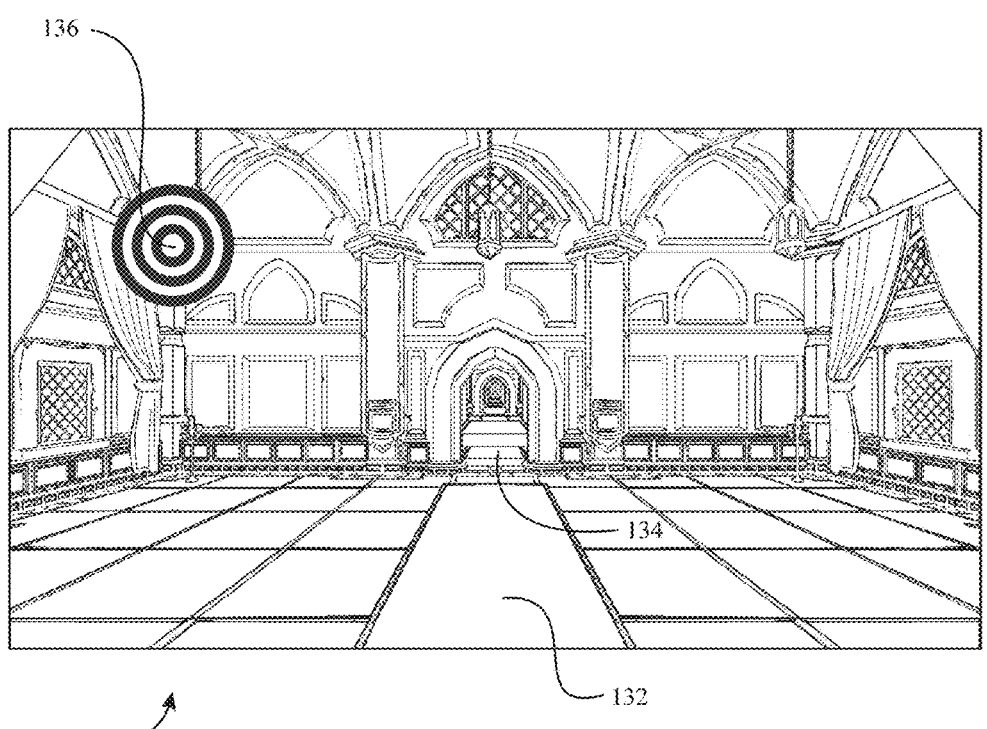
FIG. 20 is still another screen image of the immersive castle scene of FIG. 17, wherein a target is provided in the top, left-hand corner of the screen.
Figure 21:
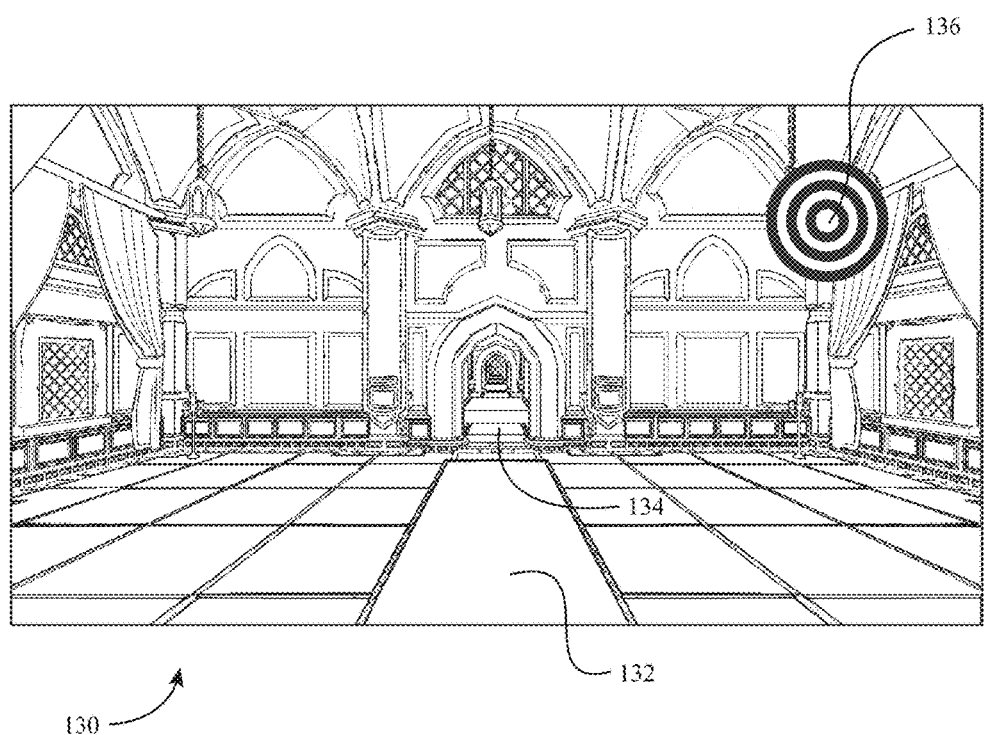
FIG. 21 is yet another screen image of the immersive castle scene of FIG. 17, wherein a target is provided in the top, right-hand corner of the screen.
Figure 22:
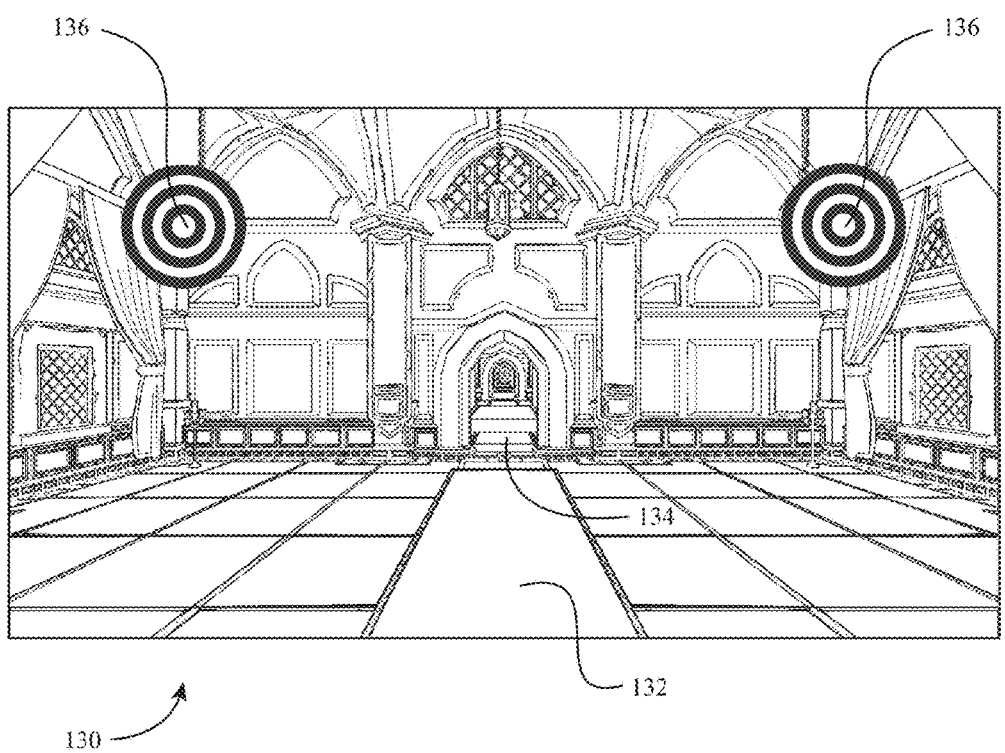
FIG. 22 is still another screen image of the immersive castle scene of FIG. 17, wherein two spaced-apart targets are provided at the top of the screen.
Figure 23:
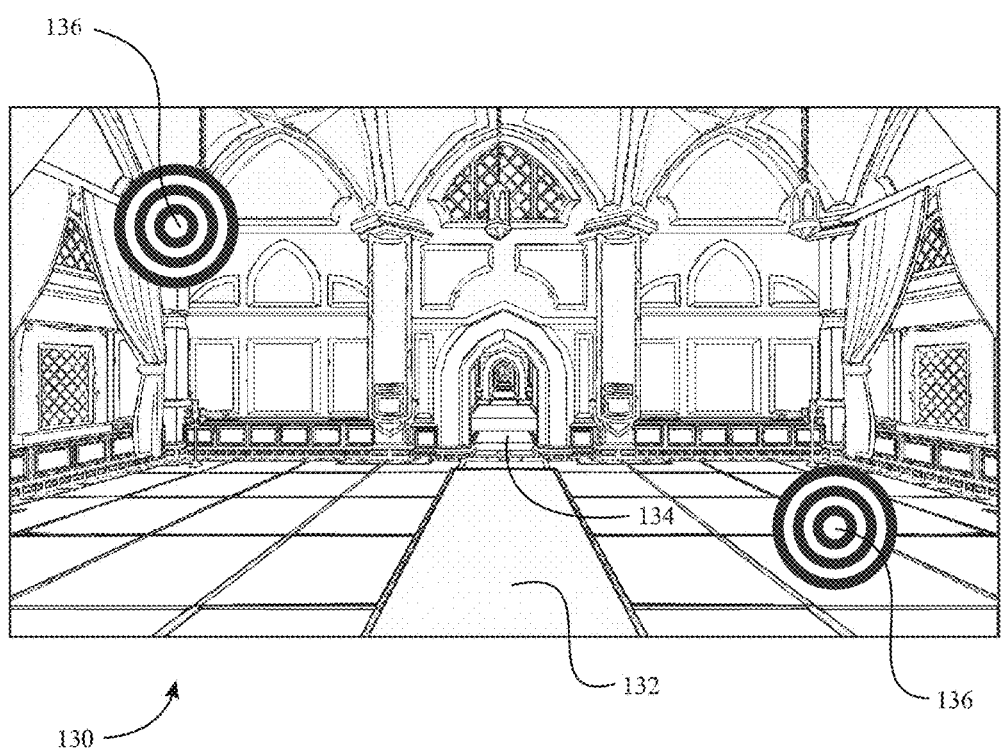
FIG. 23 is yet another screen image of the immersive castle scene of FIG. 17, wherein two targets are provided in oppositely disposed top and bottom corners of the screen.

With reference to FIGS. 17-23, an immersive castle scene in accordance with yet another illustrative embodiment of the invention will be described. Initially, with reference to FIG. 17, it can be seen that the castle screen image 130 comprises a carpeted pathway portion 132 and a tiled pathway portion 134. In the immersive castle scene, the subject progresses down the virtual pathway in the castle with the carpeted and tiled pathway portions 132, 134. The castle screen images of FIGS. 18 and 19 are substantially identical to the castle screen image 130 of FIG. 17, except that the screen image of FIG. 18 comprises a target 136 disposed in the lower, left-hand corner of the scene image, while the screen image of FIG. 19 comprises a target 136 disposed in the lower, right-hand corner of the scene image. Similarly, the castle screen images of FIGS. 20 and 21 are substantially identical to the castle screen image 130 of FIG. 17, except that the screen image of FIG. 20 comprises a target 136 disposed in the upper, left-hand corner of the scene image, while the screen image of FIG. 21 comprises a target 136 disposed in the upper, right-hand corner of the scene image. In addition, the castle screen images of FIGS. 22 and 23 are substantially identical to the castle screen image 130 of FIG. 17, except that the screen image of FIG. 22 comprises two (2) spaced-apart targets 136 disposed at the top of the scene image, while the screen image of FIG. 23 comprises two (2) spaced-apart targets 136 disposed in diagonally opposite upper and lower corners of the scene image (i.e., in the upper, left-hand corner of the screen image 130 and in the lower, right-hand corner of the screen image 130). For example, in the immersive castle scene, the subject is instructed to direct his or her gaze towards, or point at one of the targets 136 in the scene image 130. In the immersive castle scene, if the subject is determined to be gazing in the direction of the target 136 and/or pointing at the target 136, the treadmill belt speed is set to, or remains at the current treadmill belt speed in the manner described above. However, if the subject is determined to be gazing in an incorrect direction (i.e., in a direction not directed at the target), the treadmill belt speed will be reduced by a predetermined amount in the manner described above so as to make it easier for the subject to properly focus on the target 136. When two (2) spaced-apart targets 136 are disposed on the screen, as in FIGS. 22 and 23, the subject may be instructed to gaze and/or point in the direction of the targets 136 in succession. That is, initially the subject may be asked to gaze and/or point in the direction of the first target, and then subsequently, the subject may be asked to gaze and/or point in the direction of the second target. Also, similar to the immersive island scene described above, the treadmill belt speed may be modified in accordance with the ground surface type in the immersive castle scene of FIGS. 17-23. For example, when the subject walks across the carpeted pathway portion 132 of the pathway in the castle, the user-developed application software 78, sets the variable "grd_surface" to a value "2" indicative of a carpeted surface, which in turn, results in the treadmill belt speed assuming its intermediate setting, as described above. When the subject walks across the tiled pathway portion 134 of the pathway in the castle, the user-developed application software 78, sets the variable "grd_surface" to a value "3" indicative of a pavement surface, which in turn, results in the treadmill belt speed assuming its highest setting, as described above.

In the exemplary embodiment, when the motion base 52 is provided as part of the force measurement system 200, the motion base 52 may displace the instrumented treadmill 10' disposed thereon in accordance with the scene being displayed on the spherical screen 31 of the visual display device 30. For example, if an inclined ground surface is being displayed in the scene, then the instrumented treadmill 10' may be tilted by the motion base 52 so that it assumes an inclined position corresponding to the inclined ground surface in the scene. As another example, if a collision occurs in the scene (i.e., walking into a wall, etc.), then the motion base 52 may respond to the scene collision and/or the belt speed of the instrumented treadmill 10' may be reduced to zero in response to the scene collision.

In the illustrative embodiment, the data acquisition/data processing device 60 of the force measurement systems 100, 200 may generate two different types of auditory feedback that is capable of being delivered to the subject, namely discrete auditory feedback and continuous auditory feedback (sonification). Discrete auditory feedback is simpler to interpret for subjects with neurological disorders, but for some, it may be so easy that their brain stops recognizing it. As such, in the illustrative embodiment, both types of auditory feedback are provided. For example, a discrete signal in the form of a beep or gong is delivered to the subject after every mile that is traveled by the subject on the instrumented treadmill 10, 10'. In this same example, the sonification feedback results in changing some sound parameter (rhythm/pitch) based on the movement, such as a background score with changing rhythm and/or pitch as per change in belt speed.

As shown in FIGS. 1-6, in the illustrative embodiment, a pair of speakers 25 may be used to deliver the auditory feedback to the subject disposed on the instrumented treadmill 10, 10'. In the illustrative embodiment, the left speaker 25 delivers auditory feedback to the subject regarding the left side movement of the subject (e.g., auditory feedback regarding the movement of the subject's left leg), while the right speaker 25 delivers auditory feedback to the subject regarding the right side movement of the subject (e.g., auditory feedback regarding the movement of the subject's right leg). As mentioned above, the auditory feedback may be in the form of a discrete signal and/or a continuous signal. For example, a scenario using a discrete auditory signal may involve a subject walking on the treadmill while the number of miles traversed by the subject is tracked by the system 100, 200. In this scenario, a goal may be set for the number of miles (e.g., after every mile, a discrete auditory feedback in the form of a beep/gong or any other suitable sound may be emitted by the speakers 25). As another example, a scenario using a continuous auditory signal may involve a subject walking on the treadmill in a self-paced mode (i.e., in the self-paced mode, the speed of the treadmill is consistently varied over time in order to ensure that the subject is centered in a longitudinal direction of the treadmill belt). In this scenario, a continuous sound is emitted by the speakers 25, but as the subject's speed changes, different parameters of the continuous auditory signal are modified, such as the volume or pitch of the sound.

Also, in the self-paced mode, the data acquisition/data processing device 60 may be programmed such that the optic flow is also self-paced. In particular, when the subject is walking through any scene on the visual display device 30 in the self-paced mode, the optic flow is set based on the speed of the treadmill 10, 10' (i.e., the optic flow is synchronized with the speed of the treadmill 10, 10'). This way, the optic flow is also self-paced and user-controlled.

The varying levels of difficulty in the exemplary embodiment may be created by varying the belt speed of the instrumented treadmill 10, 10'. That is, the higher the level of difficulty, the greater the belt speed. Also, the belts speed of the instrumented treadmill 10, 10' may correspond to different ground surface types displayed on the spherical screen 31 of the visual display device 30. For example, when a subject is first beginning the testing or training routine, a scene containing a standard solid ground surface may be displayed on the spherical screen 31 of the visual display device 30. During this initial part of the testing or training routine, the treadmill belt speed is at a first speed setting (e.g., a low speed setting). Although, later in the testing or training routine, a scene containing more challenging ground surface, such as irregular gravel, may be displayed on the spherical screen 31 of the visual display device 30. During this latter part of the testing or training routine, the treadmill belt speed is at a second speed setting than is higher than the initial speed setting so that it is more challenging for the subject. Also, in the exemplary embodiment, certain treadmill speeds and certain ground surfaces may indicate different levels of difficulty, which can be accessible only after completing a predetermined number of miles on the treadmill. As another example, the scene displayed on the spherical screen 31 of the visual display device 30 may comprise one or more obstacles therein that become increasing more difficult as the testing or training routine progresses over time (e.g., a virtual obstacle that is placed in front of the subject may become larger with increasing levels of difficulty so that it becomes increasingly more difficult for the subject to step over, or maneuver around the obstacle).

In the exemplary embodiment, the head movement tracking system or the eye movement tracking system may be used an input device to select different paths in the scene on the spherical screen 31 of the visual display device 30. For example, the subject may be given all three (3) of the following options for selecting a particular path in the visual world: (i) remote control, (ii) head tracker, and (iii) eye tracker. For example, if the subject rotates his or her head to the left, the head tracker and/or eye tracker detects the left-pointing orientation of the subject's head, and selects a path in the visual scene that corresponds to this left position (e.g., a path on the left side of the visual scene). As such, in these embodiments, the subject may navigate through the immersive scenario using the head tracker and/or eye tracker.

In one further embodiment, the data acquisition/data processing device 60 (i.e., the operator computing device) generates a virtual reality environment with an avatar, and displays the virtual reality environment with the avatar on the spherical screen 31 of the visual display device 30. For example, the immersive virtual reality environment may comprise a scenario wherein an avatar is shown walking along a bridge or down an aisle of a grocery store. The avatar image displayed on the screen 31 represents, and is manipulated by the subject disposed on the instrumented treadmill 10, 10'. The animated movement of the avatar image on the screen 31 is controlled based upon the positional information acquired by the motion capture system described above, as well as the force and/or moment data acquired from the instrumented treadmill 10, 10'. In other words, an animated skeletal model of the subject is generated by the data acquisition/data processing device 60 using the acquired data from the motion capture system and the instrumented treadmill 10, 10'. The data acquisition/data processing device 60 then uses the animated skeletal model of the subject to control the movement of the avatar image on the spherical screen 31 of the visual display device 30. The avatar image is created on the screen 31 by the data acquisition/data processing device 60 mapping the actual coordinates of the testing or training environment into the virtual world that is displayed on the screen 31.

In another further embodiment, the data acquisition/data processing device 60 (i.e., the operator computing device) may generate a screen image with one or more visual perturbations, and display the screen image with the one or more visual perturbations on the spherical screen 31 of the visual display device 30. For example, in one exemplary embodiment, the perturbation screen image may comprise a substantially blank screen that oscillates back-and-forth (i.e., shakes back-and-forth) so as to perturb the subject while he or she is disposed on the instrumented treadmill 10, 10'.

It is readily apparent that the embodiments of the force measurement system 100, 200 described above offer numerous advantages and benefits. First of all, the embodiments of the force measurement system 100, 200 explained herein include an immersive visual display device 30 that enables a subject being tested to become fully immersed in a virtual reality scenario or an interactive game. In addition, the embodiments of the force measurement system 100, 200 described above are capable of fully immersing a subject in a virtual reality environment, yet compact enough to fit in typical building spaces.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A force measurement system, comprising:
a force measurement assembly configured to receive a subject, the force measurement assembly including:
a top surface for receiving at least one portion of the body of the subject; and
at least one force transducer, the at least one force transducer configured to sense one or more measured quantities and output one or more signals that are representative of forces and/or moments being applied to the top surface of the force measurement assembly by the subject;
at least one visual display device having an output screen configured to at least partially circumscribe three sides of a torso of the subject, the at least one visual display device configured to display one or more scenes on the output screen so that the scenes are viewable by the subject, wherein the one or more scenes are configured to create a simulated environment for the subject, and wherein the output screen of the at least one visual display device comprises a bottom edge and a top edge;
one or more data processing devices operatively coupled to the force measurement assembly and the at least one visual display device, the one or more data processing devices configured to receive the one or more signals that are representative of the forces and/or moments being applied to the top surface of the force measurement assembly by the subject, and to convert the one or more signals into output forces and/or moments, the one or more data processing devices further configured to dynamically increase or decrease a speed of one or more displaceable components of the force measurement system in accordance with a visual element of the one or more scenes that are displayed on the output screen of the at least one visual display device while the subject navigates through the one or more scenes of the simulated environment on the output screen of the at least one visual display device;
wherein the visual element of the scene that is displayed on the output screen of the at least one visual display device comprises an obstacle disposed in a virtual walking path of the subject; and
wherein the one or more data processing devices are further configured to determine whether a foot of a virtual representation of the subject on the output screen clears the obstacle, and when the foot of the virtual representation of the subject does not clear the obstacle, generate and display a visual indicator on the output screen of the at least one visual display device that is indicative of the height that the foot must achieve to clear the obstacle.

2. The force measurement system according to claim 1, wherein the at least one visual display device comprises a concavely shaped projection screen having a cylindrical middle portion, a spherical bottom portion, and a spherical top portion, the cylindrical middle portion being disposed above the spherical bottom portion and below the spherical top portion, the cylindrical middle portion having a continuous curvature between first and second opposed side edges of the concavely shaped projection screen, wherein the cylindrical middle portion of the concavely shaped projection screen results in a focal region for a subject disposed on the force measurement assembly, rather than any one single focal point, so that an immersion experience for the subject is substantially unaffected by a height of the subject.

3. The force measurement system according to claim 2, wherein the concavely shaped projection screen comprises a plurality of screen sections that are attached to one another so as to form the overall screen.

4. The force measurement system according to claim 1, wherein the force measurement assembly is in the form of an instrumented treadmill.

5. The force measurement system according to claim 4, wherein the force measurement system further comprises a motion base disposed underneath the instrumented treadmill, the motion base configured to displace the instrumented treadmill in one or more directions.

6. The force measurement system according to claim 1, wherein the output screen of the at least one visual display device further comprises an overhanging top portion and a top cutout defining a cutout footprint; and
wherein the force measurement system further comprises a motion capture system operatively coupled to the one or more data processing devices, the motion capture system comprising at least one motion capture device configured to detect the motion of one or more body gestures of the subject, and the at least one motion capture device being disposed within the cutout footprint of the top cutout of the output screen of the at least one visual display device.

7. The force measurement system according to claim 6, wherein the at least one motion capture device comprises a plurality of motion capture devices, a subset of the plurality of motion capture devices being circumferentially spaced apart around the top cutout of the output screen of the at least one visual display device, and the subset of the plurality of motion capture devices being disposed within the cutout footprint.

8. The force measurement system according to claim 6, wherein the one or more data processing devices are configured to adjust the one or more scenes on the output screen of the at least one visual display device in accordance with the detected motion of the one or more body gestures of the subject by the at least one motion capture device, wherein the one or more body gestures of the subject comprise at least one of: (i) one or more limb movements of the subject, (ii) one or more torso movements of the subject, and (iii) a combination of one or more limb movements and one or more torso movements of the subject.

9. The force measurement system according to claim 8, wherein the at least one motion capture device comprises a plurality of motion capture devices, and the plurality of motion capture devices of the motion capture system are in the form of a plurality of cameras, the plurality of cameras configured to capture the motion of the subject.

10. The force measurement system according to claim 9, wherein a first subset of the plurality of cameras of the motion capture system are disposed above the subject, and wherein a second subset of the plurality of cameras of the motion capture system are disposed behind the subject.

11. The force measurement system according to claim 10, wherein the first subset of the plurality of cameras of the motion capture system are attached to the output screen of the at least one visual display device or to a screen support structure that supports the output screen of the at least one visual display device; and
wherein the second subset of the plurality of cameras of the motion capture system are attached to one of: (i) the output screen of the at least one visual display device, (ii) a screen support structure that supports the output screen of the at least one visual display device, and (iii) a camera mounting structure that is attached to the output screen of the at least one visual display device or to the screen support structure.

12. The force measurement system according to claim 1, wherein the top surface of the force measurement assembly is disposed above the bottom edge of the output screen of the at least one visual display device, and the bottom edge of the output screen of the at least one visual display device is spaced apart from a floor on which the at least one visual display device is supported by one or more screen support members, the one or more screen support members being spaced apart from the top surface of the force measurement assembly that is configured to receive the at least one portion of the body of the subject.

13. The force measurement system according to claim 1, further comprising an input device operatively coupled to the one or more data processing devices, the input device configured to enable the subject to select different navigation paths in the one or more scenes of the simulated environment on the output screen of the at least one visual display device.

14. The force measurement system according to claim 13, wherein the input device that is configured to enable the subject to select different navigation paths in the one or more scenes of the simulated environment on the output screen of the at least one visual display device comprises an eye position tracking device or a head position tracking device.

15. A force measurement system, comprising:
a force measurement assembly configured to receive a subject, the force measurement assembly including:
one or more displaceable components, the one or more displaceable components having one or more respective surfaces for receiving one or more respective limbs of the subject; and
at least one force transducer, the at least one force transducer configured to sense one or more measured quantities and output one or more signals that are representative of one or more loads being applied to the one or more respective surfaces of the one or more displaceable components by the subject;
at least one visual display device having an output screen, the at least one visual display device configured to display a scene on the output screen so that the scene is viewable by the subject;
a pointing or gaze direction determination device configured to determine a pointing direction or gaze direction of the subject, the pointing or gaze direction determination device being external to the at least one visual display device; and
one or more data processing devices operatively coupled to the at least one force transducer of the force measurement assembly, the at least one visual display device, and the pointing or gaze direction determination device, the one or more data processing devices configured to receive the one or more signals that are representative of the forces and/or moments being applied to the one or more respective surfaces of the one or more displaceable components by the subject, and to convert the one or more signals into output forces and/or moments, the one or more data processing devices further configured to generate at least a first visual element and a second visual element, and to display the first visual element and the second visual element in the scene on the output screen of the at least one visual display device, the one or more data processing devices additionally configured to control the displacement of the one or more displaceable components of the force measurement assembly in accordance with the first visual element of the scene that is displayed on the output screen of the at least one visual display device, the one or more data processing devices further configured to determine a manner in which the subject interacts with the second visual element of the scene and to adjust the displacement of the one or more displaceable components of the force measurement assembly based upon the interaction of the subject with the second visual element during a subject testing or training routine, the second visual element of the scene that is displayed on the output screen of the at least one visual display device comprising at least one virtual target, and the one or more data processing devices additionally configured to determine the manner in which the subject interacts with the second visual element of the scene by determining when the pointing direction or the gaze direction of the subject, as determined by the pointing or gaze direction determination device, coincides with the at least one virtual target displayed on the output screen, and when the pointing direction of the subject does not coincide with the at least one virtual target displayed on the output screen;
wherein, when the pointing direction of the subject coincides with the at least one virtual target displayed on the output screen during the subject testing or training routine, the one or more data processing devices are further configured to maintain a current speed of the one or more displaceable components of the force measurement assembly;
wherein, when the pointing direction of the subject does not coincide with the at least one virtual target displayed on the output screen during the subject testing or training routine, the one or more data processing devices are further configured to decrease the speed of the one or more displaceable components of the force measurement assembly below the current speed of the one or more displaceable components of the force measurement assembly so as to make it easier for the subject to properly focus on the at least one virtual target during the subject testing or training routine;
wherein the first visual element of the scene that is displayed on the output screen of the at least one visual display device comprises an obstacle disposed in a virtual walking path of the subject; and
wherein the one or more data processing devices are further configured to determine whether a foot of a virtual representation of the subject on the output screen clears the obstacle, and when the foot of the virtual representation of the subject does not clear the obstacle, generate and display a visual indicator on the output screen of the at least one visual display device that is indicative of the height that the foot must achieve to clear the obstacle.

16. The force measurement system according to claim 15, wherein the force measurement assembly is disposed on a motion base, the motion base configured to displace the force measurement assembly in one or more directions.

17. The force measurement system according to claim 15, wherein the force measurement assembly is in the form of an instrumented treadmill and the one or more displaceable components are in the form of one or more treadmill displaceable elements of the instrumented treadmill; and wherein the one or more data processing devices are further configured to adjust a rotational speed of the one or more treadmill displaceable elements in accordance with the first visual element of the scene that is displayed on the output screen of the at least one visual display device.

18. The force measurement system according to claim 17, wherein the first visual element of the scene that is displayed on the output screen of the at least one visual display device comprises a ground surface element; and wherein the one or more data processing devices are further configured to dynamically increase or decrease the rotational speed of the one or more treadmill displaceable elements in accordance with a type of the ground surface element of the scene that is displayed on the output screen of the at least one visual display device.

19. The force measurement system according to claim 17, wherein the one or more data processing devices are further configured to dynamically decrease the rotational speed of the one or more treadmill displaceable elements when the virtual representation of the subject on the output screen collides with the obstacle disposed in the virtual walking path of the scene that is displayed on the output screen of the at least one visual display device.

20. The force measurement system according to claim 19, wherein the virtual representation of the subject on the output screen of the at least one visual display device comprises an avatar controlled by one or more body gestures of the subject as detected by the force measurement assembly and a motion detection system.

21. The force measurement system according to claim 19, wherein the one or more data processing devices are further configured to compute a center of pressure for the subject as a function of the output forces and/or moments determined from the one or more signals of the force measurement assembly, and to control a movement of the virtual representation of the subject on the output screen of the at least one visual display device using the computed center of pressure.

22. The force measurement system according to claim 15, wherein the pointing or gaze direction determination device comprises at least one of the following devices: (i) an eye position tracking device configured to track a position of one or more eyes of the subject, (ii) a head position tracking device configured to track a position of the head of the subject, and (iii) a pointing device configured to indicate an aiming direction of a body portion of the subject.

23. The force measurement system according to claim 22, wherein the one or more data processing devices are further configured to control a navigation of the virtual representation of the subject on the output screen of the at least one visual display device in accordance with an output signal from at least one of the eye position tracking device, the head position tracking device, and the pointing device.

24. The force measurement system according to claim 15, wherein the at least one virtual target that is generated by the one or more data processing devices and displayed on the output screen of the at least one visual display device comprises a plurality of targets spaced apart on the output screen of the at least one visual display device; and wherein the one or more data processing devices are further configured to determine whether the subject sequentially points in respective directions of each of the plurality of targets.

25. The force measurement system according to claim 15, wherein, during the subject testing or training routine, when the pointing direction of the subject coincides with the at least one virtual target displayed on the output screen, the one or more data processing devices are further configured to set a target focus variable to a first value;

wherein, during the subject testing or training routine, when the pointing direction of the subject does not coincide with the at least one virtual target displayed on the output screen, the one or more data processing devices are further configured to set the target focus variable to a second value that is different from the first value; and wherein the one or more data processing devices are further configured to maintain the current speed of the one or more displaceable components of the force measurement assembly when the target focus variable equals the first value, and wherein the one or more data processing devices are further configured to decrease the speed of the one or more displaceable components of the force measurement assembly below the current speed of the one or more displaceable components of the force measurement assembly when the target focus variable equals the second value.

* * * * *